(12) United States Patent
Takahashi et al.

(10) Patent No.: US 7,160,511 B2
(45) Date of Patent: Jan. 9, 2007

(54) LIQUID PIPETTING APPARATUS AND MICRO ARRAY MANUFACTURING APPARATUS

(75) Inventors: Seiya Takahashi, Hachioji (JP); Morinao Fukuoka, Sagamihara (JP)

(73) Assignee: Olympus Corporation, Tokyo (JP)

( * ) Notice: Subject to any disclaimer, the term of this patent is extended or adjusted under 35 U.S.C. 154(b) by 189 days.

(21) Appl. No.: 09/784,977

(22) Filed: Feb. 16, 2001

(65) Prior Publication Data

US 2001/0036424 A1  Nov. 1, 2001

(30) Foreign Application Priority Data

| Feb. 18, 2000 | (JP) | ............................ 2000-041578 |
| Feb. 22, 2000 | (JP) | ............................ 2000-044547 |
| Sep. 20, 2000 | (JP) | ............................ 2000-284854 |

(51) Int. Cl.
  *B01L 3/02* (2006.01)
  *G01N 1/10* (2006.01)
(52) U.S. Cl. ...................... 422/100; 422/919; 422/926; 422/922; 436/180; 73/86.32; 73/863.44; 73/863.54; 73/864; 73/864.01; 73/864.11; 73/864.31
(58) Field of Classification Search ............... 422/100, 422/926, 919, 922; 436/180; 73/863.32, 73/863.33, 863.44, 863.52, 863.54, 864, 73/864.01, 864.11, 864.13, 864.16, 864.17, 73/864.25, 864.31
See application file for complete search history.

(56) References Cited

U.S. PATENT DOCUMENTS

| 4,546,361 | A   |   | 10/1985 | Brescia et al. |
| 4,730,631 | A   | * | 3/1988  | Schwartz ..................... 134/155 |
| 5,316,726 | A   | * | 5/1994  | Babson et al. ................ 422/65 |
| 5,439,649 | A   | * | 8/1995  | Tseung et al. ................ 422/99 |
| 5,443,792 | A   | * | 8/1995  | Buhler ......................... 422/67 |
| 5,474,744 | A   | * | 12/1995 | Lerch .......................... 422/100 |
| 5,525,302 | A   | * | 6/1996  | Astle ........................... 422/100 |
| 5,593,893 | A   | * | 1/1997  | Kobashi et al. ............... 436/50 |
| 5,763,278 | A   |   | 6/1998  | Sickinger et al. |
| 5,770,151 | A   | * | 6/1998  | Roach et al. ................. 422/63 |
| 5,807,522 | A   |   | 9/1998  | Brown et al. |
| 5,854,645 | A   |   | 12/1998 | Witteveen et al. |
| 5,879,944 | A   | * | 3/1999  | Komatsu ...................... 436/50 |
| 5,927,547 | A   |   | 7/1999  | Papen et al. |
| 5,948,359 | A   | * | 9/1999  | Kalra et al. ................... 422/65 |
| 5,948,360 | A   | * | 9/1999  | Rao et al. ..................... 422/65 |
| 5,957,167 | A   | * | 9/1999  | Feygin ......................... 141/31 |
| 6,105,636 | A   | * | 8/2000  | Scatizzi et al. ............. 141/130 |
| 6,116,297 | A   | * | 9/2000  | Feygin ......................... 141/31 |
| 6,132,582 | A   | * | 10/2000 | King et al. .................. 204/604 |
| 6,255,119 | B1  | * | 7/2001  | Baier ........................... 436/180 |
| 6,309,891 | B1  | * | 10/2001 | Shalon et al. ............... 436/180 |
| 6,426,225 | B1  | * | 7/2002  | Lewis et al. ................... 436/8 |

(Continued)

FOREIGN PATENT DOCUMENTS

EP      0 895 082 A2    2/1999

(Continued)

*Primary Examiner*—Brian R. Gordon
(74) *Attorney, Agent, or Firm*—Scully, Scott, Murphy & Presser PC

(57) ABSTRACT

A liquid pipetting apparatus for dispensing liquid of minute volume for use in a survey instruments of a hemanalysis machine, a genetic screening, and a pharmaceutical screening, etc., is disclosed. The liquid pipetting apparatus comprises a liquid holding member for holding the liquid, and capable of dispensing the liquid from one end, and a driving member for moving the liquid holding member forward and backward along the dispensing direction, the liquid holding member being moved by the driving means, thereby dispensing the liquid held on the liquid holding member.

20 Claims, 29 Drawing Sheets

U.S. PATENT DOCUMENTS

| | | | |
|---|---|---|---|
| 6,521,187 B1 * | 2/2003 | Papen | 422/100 |
| 6,551,557 B1 * | 4/2003 | Rose et al. | 422/100 |
| 6,558,623 B1 * | 5/2003 | Ganz et al. | 422/63 |
| 6,576,477 B1 * | 6/2003 | Tokiwa et al. | 436/180 |
| 6,672,344 B1 * | 1/2004 | Stokes et al. | 141/234 |
| 2001/0026772 A1 * | 10/2001 | Fuerst et al. | 422/64 |
| 2002/0173048 A1 * | 11/2002 | Nakazawa et al. | 436/180 |
| 2003/0087442 A1 * | 5/2003 | Popa-Burke et al. | 436/43 |

FOREIGN PATENT DOCUMENTS

| | | |
|---|---|---|
| JP | 6-347305 | 12/1994 |

* cited by examiner

FIG. 16
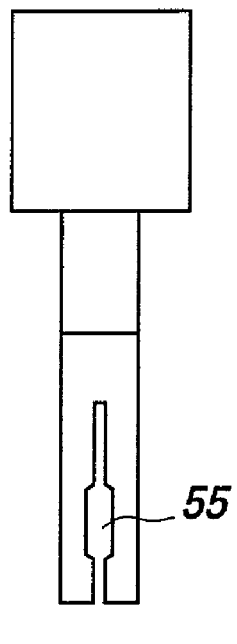
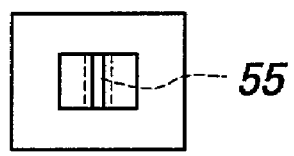
FIG. 17
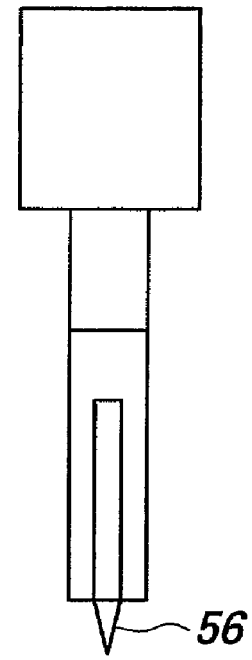
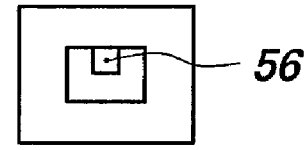

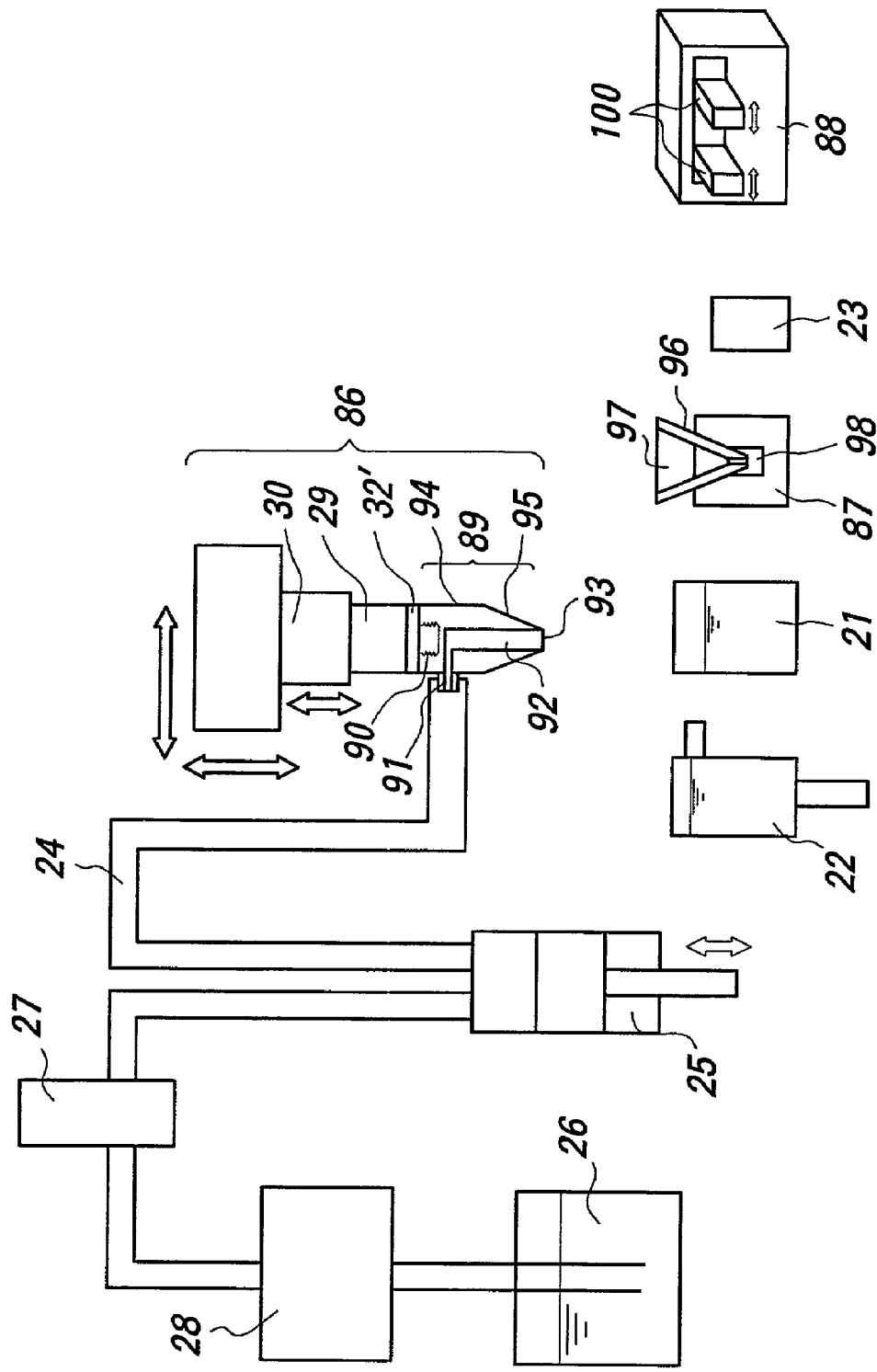

FIG. 31a  FIG. 31b  FIG. 31c
FIG. 31d
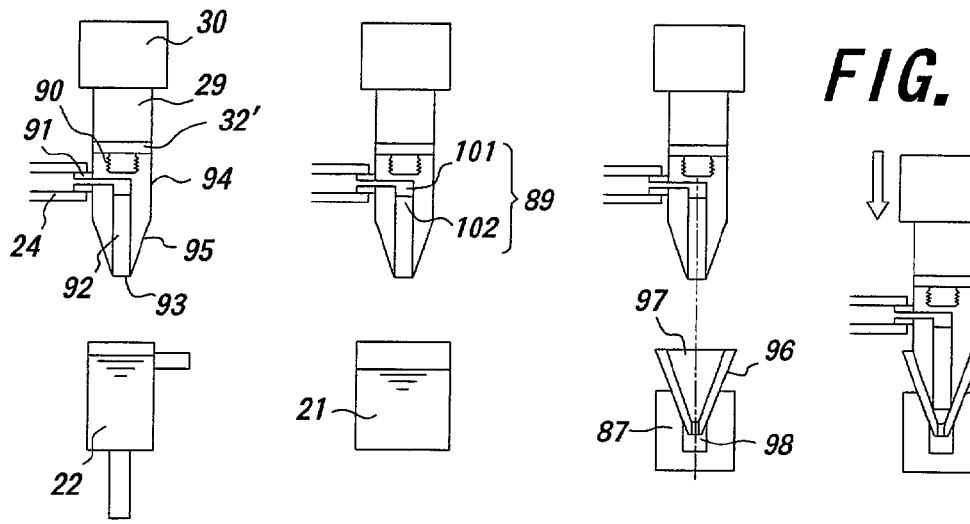
FIG. 31e  FIG. 31f  FIG. 31g
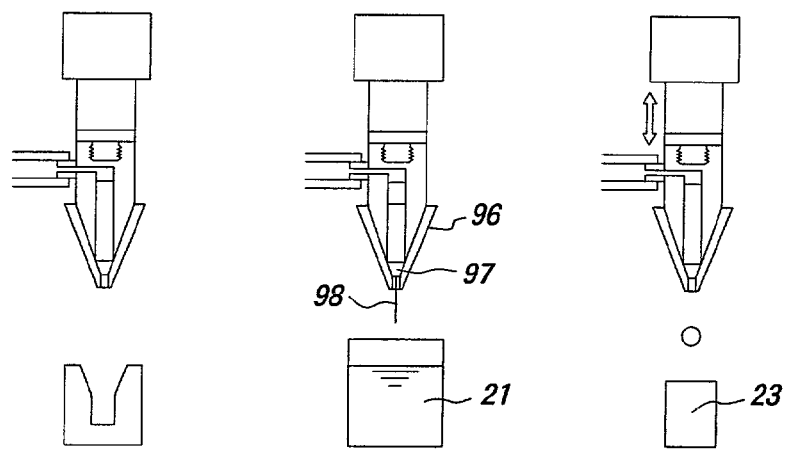
FIG. 31h  FIG. 31i  FIG. 31j
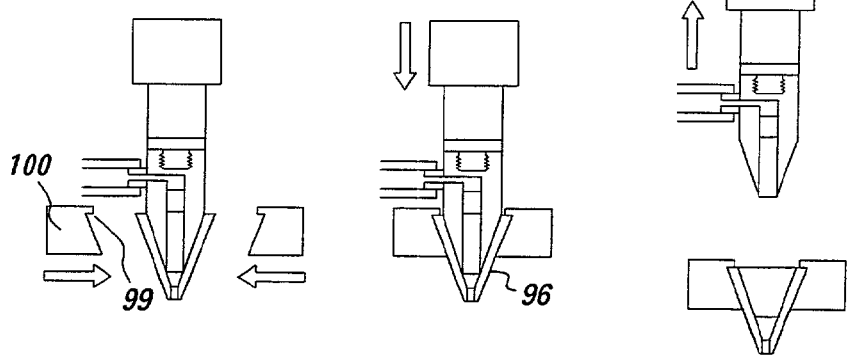

LIQUID PIPETTING APPARATUS AND MICRO ARRAY MANUFACTURING APPARATUS

BACKGROUND OF INVENTION

1. Technological Field to which Invention Belongs

The present invention relates to a liquid pipetting apparatus, which dispenses and pipettes a liquid of small volume, for example, liquids such as reagents and molten metals, and an array manufacturing apparatus, which manufactures the array constituted by arranging the spot of the liquid including a probe on a substrate in a matrix shape with high density.

2. Relating Technology

Survey instruments of a hemanalysis machine, a genetic screening, and a pharmaceutical screening, etc. are requested to reduce the volume of the waste fluid for the running cost reduction. The volume of the waste fluid is chiefly constituted from two of reactive test solutions and washing water for reactive containers, so that the volume of a reactive test solution should be made reduced in order to reduce this waste fluid. A reactive test solution is decided according to a minimum dispense volume of a liquid dispensing device, so that it is effective to make a minimum dispense volume a minute volume for the reduction in volume of the waste fluid.

Moreover, these survey instruments are required to decrease the inspection time in order to make an increase in volume of the inspection and the inspection item in recent years correspondent. It is effective to decrease the required time to the chemical reaction process of a reactive test solution to shorten the inspection time, but to this end, a minimum dispense volume should be made a minute volume, and the constructed reactive test solution should be made minimized. In addition, micro array attracts attention as a new genetic screening technology in recent years. Micro array is a chip which utilized to arrange the liquid of a liquid sample containing the fragment of various micro array on the substrate in the matrix shape, to react it with the reagent and to observe the reactive result with the fluorometry or the like. For the micro array, a liquid sample can be arranged on the substrate with a high density by making the volume of a minimum charging of a liquid sample a minute volume, as a result, a many of samples can be analyzed at a time, so that the minute volume making of the volume of a minimum charging leads to shortening the analysis time.

In this way, it is required to make a minimum dispense volume a minute volume for reducing the volume of the waste fluid and shortening the inspection time in various survey instruments and analyzer used for the medical treatment field.

In the past, the syringe piston pump has been used as a liquid dispense technology of such a survey instrument. However, there is a problem that the volume of a minimum dispense of the syringe piston pump is about 2 μL, and the dispense precision becomes deteriorated extremely when the liquid of small volume or more from this was dispansed. As for such a problem, a nanopipette, which applies the ink jet method as a technology for reducing the volume of a minimum dispense by two digits or more with comparison to the conventional method, is shown in for example Japanese Patent Application Opened No. 8-233710.

FIG. 44 shows a schematic block diagram to which the main portion of the nanopipette in the ink jet method is shown by the cross-section.

In FIG. 44, this main portion comprises a pipette chamber 152 formed in a pipette frame 151, a nozzle 153 communicated to the atmosphere, for generating and dispensing the liquid, a reservoir 154, a piezo-electric element 156 to supply driving force to the pipette chamber 152 through a diaphragm 155, a controller 157 for controlling the piezo-electric element, and Ian introduction entrance 158 where reagent or sample is introduced into the reservoir 154.

In the conventional embodiment, an apparatus, which makes a reactive sample of the liquid by mixing a specimen sample and a necessary reagent, comprises a pipette element capable of generating the liquid by which the volume, which does not exceed 0.1 nl, is assumed to be a unit, there is proposed a proposal adopting an ink jet method which performs a pipetting of a reagent and a reactive sample necessary to construct a liquid reactive sample with an volume which does not exceed least 1 nl and with a unit which does not exceed resolution of 0.1 nl.

The dispensing speed of this pipette can be raised in proportion to the frequency of the high-frequency wave by which the acceleration power is driven, for example, in case of driving it by 10 kHz, the construction of one reaction sample can be achieved in case of driving it with 10 kHz in the maximum for example in about 1 sec. per 1 μl. As a result, a reactive sample can be constructed with high speed such as in 100 samples per one minute-two minutes.

However, in the prior art, the acceleration applying element such as piezo-electric elements gives liquid the acceleration power directly or through the partition such as diaphragms indirectly, so that in the case that the piezo-electric element touches the liquid directly, there is a problem that the feature of washing the conduit becomes difficult since a liquid sample intrude in the crystal grain field on the surface of the piezo-electric element. Moreover, in case of having the partition such as diaphragms, there is a problem that the structure comes to complicate, and as a result, the manufacturing cost rises.

Moreover, in the case that the bubble is generated in the chamber with reference to the evaporation of the cavitation and dissolved oxygen etc., the problem that the pressure generated by the acceleration applying element attenuates with the bubble, and the liquid cannot be charged, generates.

In addition, the feature of making plural arrays of pipettes can became possible by adopting the above system. That is, a chamber, a reservoir, and driving element are small size in the pipette of the system, and the voltage is only applied to the piezo-electric element whose drive mechanism is also a driving element, so that the controlling mechanism is also simple and can also drive a plural driving elements easily, and independently. By mounting the arrayed pipette to a suitable movement element, and driving the piezo-electric element as driving element of a necessary pipette portion while properly changing a relative position with a reactive container where plural reactive holes are arranged on the plane according to necessary timing, the feature of achieving the pipette of the object reagent became possible with high throughput for a reactive hole at the object position so as to just draw by the ink-jet printer.

The hemanalysis machine, the genetic screening, and the pharmaceutical screening or the like are measured by making a liquid sample which contains a chemical compound, blood and DNA or the like react chemically, and by measuring the result of the reaction with the use of the fluorometry and the spectrophotometer or the like. Therefore, there is a problem that when impurities influencing on the chemical reaction are mixed with the liquid sample, an accurate inspection result can not be obtained.

In order to prevent such a problem, there is devised that the dispensing device is used as disposable, and the dispensing device is changed in case of dispensing a different kind of liquid sample. If such a system is adopted, impurities might not mix with the conduit. However, the inspection machine of the pharmaceutical screening etc. handles the kind of liquid sample of several thousand from several hundreds, so that the method of exchanging the dispensing device whenever the liquid sample is changed, is not realistic in plane of the cost. Moreover, the prior art uses the piezo-electric element as an actuator, but if the influence on the environment is considered since the piezo-electric element contains a large volume of lead, the feature of using the dispense apparatus as disposable becomes a problem. In order to resolve these problems, the actuator and the conduit are constructed detachably, if only the conduit may be exchanged when the liquid sample is exchanged the component to be abandoned is only the conduit, so that the cost becomes cheap and the adverse effect is not caused for the environment.

Here, in the prior art, a method of separating and detaching the actuator and the conduit is considered. In the prior art, there is utilized that the actuator of the piezo-electric element etc. supplies the acceleration power to the liquid directly, or through the shroud element such as diaphragms indirectly. In the structure that the actuator gives liquid the acceleration power directly, the actuator and the conduit cannot naturally be separated detached. On the one hand, in the structure to use the partition element such as diaphragms, if some installation and deinstallation elements to separate both between the actuator and the diaphragm are provided, the feature of detaching the actuator and the conduit becomes possible. However, the diaphragm has very thin shape to make a small displacement of few μm act on the liquid, and has the problem of easily arriving at the deformation or the breakage by little power which causes in the case of detaching works. Even if the diaphragm does not damage, the position of the diaphragm is easily displaced before and behind the detachable working due to the size error between the assembly error which causes at the detachable works and the exchanged member, as a result, the problem causes that the acceleration power, which acts on the liquid, changes and the dispense volume changes.

Moreover, in a liquid dispensing device with the use of the ink jet system, the smaller the nozzle diameter is to generate a small liquid, the more advantageous, the nozzle diameter should be made φ 0.1 mm or less to generate the liquid of at most 0.1 nl or less as in the prior art. On the other hand, the genetic screening machine and the biochemistry analysis machine or the like often contain the cell and the protein in the handled liquid sample. These liquid samples come to generate the nozzle clogging easily according to the experience of the inventor when the nozzle diameter becomes φ0.1 mm or less.

Moreover, in the case where the nozzle blocking is generated, by performing following process that the nozzle is soaked in the washing water or the like and the pressure is raised by supplying the liquid is supplied in the chamber, the work for removing the blocked substance is performed, however, there is a case by which the substance blocked in the nozzle cannot be removed even if such restoration work is done, too. Moreover, in a case that when the substance blocked in the nozzle is removed, the nozzle is damaged, the problem that the dispense volume changes before and after the nozzle blocking, may be happen, too. In case where such a problem occurs, only the nozzle has to be able to be exchanged, but in the prior art, the nozzle, the chamber, and the actuator are constituted to one body, so that the nozzle alone cannot be exchanged, and the entire dispensing device should be exchanged, and thus this invited the problem as an increase in the running cost and an increase of waste, etc.

Moreover, the liquid is supplied from the introduction entrance to the reservoir in the prior art, but the case, that the liquid is attracted from the nozzle, is not described, however, when liquid in little volume of many kinds of samples are inspected, as in the hemanalysis machine and the genetic screening machine, etc., aspirating and the dispensing systems are preferable from the viewpoint of the inspection treatment power. In the prior art, in the case of attracting the sample from the nozzle, the aspiration method is considered by installing the liquid aspiration means such as pumps behind the introduction entrance. However, a long time is required to attract the liquid from the nozzle where the caliber is as small as the prior art, so that there is a problem that the time required for the inspection becomes long, too as a result.

On the other hand, if the conduit of the dispensing device can be cleanly washed, many kinds of liquid samples can be dispensed without exchanging the conduit by the same dispensing device. In the prior art, though a general washing is performed by pouring the washing water in the conduit, but it is difficult for the flow rate in the vicinity of the pipette chamber and the reservoir to flush the sample which adheres to the surface of the conduit extremely late since the caliber of the nozzle is small even if it tries to pour the washing water from the reservoir side in the conduit.

The prior art of the manufacturing method of the micro array (probe array) is disclosed in Japanese Patent Application Laid-open No. 187900/1999. In the prior art, the spot including the probe is formed on a solid phase by adhering the liquid sample which contains the probe as the liquid drop to the solid phase (solid substrate) by the ink jet method. Hereafter, the outline of the manufacturing method of the array according to the above prior art is explained by using FIG. 45 and FIG. 46 which is the cross-sectional view on the A—A line of FIG. 45.

In FIG. 45, numeral 161 is a liquid supply system (nozzle) which can dispensably hold the liquid including probe (for example nucleic acid probe) as the dispensing liquid, numeral 163 is solid phase (for example transparent glass board) to which said nucleic acid probe should be combined, numeral 165 is a kind of the ink jet head and is a bubble jet head including a mechanism, which gives the thermal energy to the liquid and dispenses the liquid, and numeral 164 is a liquid dispensed from the bubble jet head 165 and including the nucleic acid probe.

Moreover, in the bubble jet head 165 shown in FIG. 46, numeral 167 is a liquid including the nucleic acid probe to be dispensed, and numeral 177 is a substrate section having the heat portion for giving the dispense energy to the liquid. The substrate section 177 includes a protective coat 169 formed with oxidation silicon or the like, electrodes 171-1 and 171-2 formed with aluminum or the like, a heat resistive layer 173 formed with Nichrome wire or the like, a heat storage layer 175, and a supporting body 176 formed with alumina or the like having excellent heat radiative property.

The liquid 167 containing the above nucleic acid probe, reaches a dispense orifice 179 (dispense vent), and forms meniscus 181 with the given pressure. Under such a condition, when an electric signal is applied to electrodes 171-1 and 171-2, the region (foam region) shown by a sign 183 is heated rapidly and generates heat, so that the bubble is generated in the liquid 167 touched to this region. The meniscus is dispensed by the pressure of the bubble, and liquid 167 is dispensed from the orifice 179. The dispensed liquid 167 flies toward the surface of the solid phase 163.

The volume of the liquid capable of being dispensed with the bubble jet head including the above structure is different according to the size or the like of the nozzle, but this volume can be controlled in the order of, for example, 4–50 picoliter, so that it is extremely effective as the means to arrange nucleic acid probe with high density. Moreover, in the official gazette of the above prior art, it is described that it can use the piezo jet head for dispensing the liquid in the nozzle according to utilizing the vibrating pressure of the piezo element, in place of the above bubble jet head.

The above prior art has the advantage by which the probe sample of a minute volume can be arranged on the solid phase substrate with high accuracy and with high density, but the other bubbles may be mixed in the liquid in the dispense head in addition to the bubble for dispensing the liquid, and thus in the case that the bubble mixes in the dispense head, there is a case that the volume of the dispensing liquid is changed and the dispense of the liquid can not be performed. In that case, the problem is caused that the spot diameter of the array becomes an ununiformity. That is, in the above prior art, there is a case that the bubble mixes in the conduit, occasionally, by exchanging the liquid sample and by evaporating dissolved oxygen in the liquid sample, so that in case of mixing the bubble, pressure for dispensing the liquid becomes attenuated by the mixed bubble, and thus the volume of the dispensing liquid changes.

SUMMARY OF THE INVENTION

The present invention is performed by considering the above circumstances, and has its object to provide a new possible liquid pipetting apparatus, in which while enabling a liquid dispense of small volume with high accuracy, even if the bubble is mixed in the conduit, the liquid can be dispensed, with excels in washing, and with decrease in manufacturing cost.

The present invention pays attention to the problem of the above, and has its object to provide a new liquid pipetting apparatus, in which the actuator and the conduit are detachable, and the pipetting apparatus does not change the dispense volume before and behind the detachable working, in addition, only the nozzle can be exchanged. and further shortening in sucking time of the liquid is possible.

The present invention also has for its object to provide a micro array manufacturing apparatus which can manufacture the micro array having a uniform spot diameter even in case of mixing the bubble in the dispensing conduit.

To this end, there is provided a liquid pipetting apparatus for dispensing liquid of small volume comprising a liquid holding member for holding the liquid, and capable of dispensing the liquid from one end, and a driving member for moving the liquid holding member forward and backward along the dispensing direction, the liquid holding member being moved by the driving means, thereby dispensing the liquid held on the liquid holding member.

Moreover, the liquid holding member holds the liquid in the inner portion thereof, and has a dispense vent for dispensing the liquid held inside thereof.

Further, the liquid holding portion of the liquid holding member has a taper shape of which the cross-sectional area becomes small as approaching the dispense vent In addition, a liquid pipetting system for dispensing the liquid of small volume with high accuracy dispenses the liquid by making inertia force act on the liquid, as a result of movement of the liquid holding member.

According to the liquid pipetting apparatus having the above constitution, the improvement in washing of the conduit and the decrease of the cost becomes possible. Even if the bubble exists in the conduit additionally, it can dispense the inspection sample. In addition, the liquid of a small volume can be dispensed with highly accurate. Moreover, number of man-hours required for manufacture, can be reduced, the decrease of the cost becomes possible, and washing is also good.

To this end, in the present invention, there is provided a liquid pipetting apparatus comprising a liquid holding member capable of dispensing the liquid from one end and for holding the liquid, a driving means for moving the liquid holding member, and a connecting member for connecting the liquid holding member with the driving means detachably, whereby the liquid held in the liquid holding member is dispensed by moving the liquid holding member with the driving means.

According to the present invention, the liquid holding member is connected to the driving means detachably.

Moreover, in the liquid pipetting apparatus, the liquid is dispensed by rapidly moving the liquid holding member in the direction opposite to the dispensing direction of the liquid by the driving member.

Also, in the Liquid pipetting apparatus, the liquid is dispensed by moving the liquid holding member in the dispensing direction of the liquid and by stopping it rapidly.

In the prior art, the acceleration is acted on the liquid by decreasing the conduit volume, but according to the present invention, an inertia force is made to act on the inspection sample, by giving the acceleration to the liquid holding member, thereby dispensing the liquid, so that the connection between the liquid holding member and the driving means can be formed with the solid body detachably. As a result, the connection between the driving means and the liquid holding member can be performed detachably, and a liquid dispensing device which does not change the dispense volume before and after the detaching works, can be provided. Moreover, the feature of dispensing plural inspection samples will become possible in a short time. In addition, the number of driving means can be decreased, so that the simplification of the controller of the driving means becomes possible. Further, the feature of shortening the aspirating time becomes possible since the inspection sample is aspirated at the aspirating vent where caliber are larger than dispense vent. Moreover, the conduit member and the nozzle member can be detached with the nozzle installation and deinstallation mechanism, and the flow rate of the washing water in the liquid holding member can be made fast, and therefore the improvement of the washing efficiency becomes possible.

To achieve the above object, the present invention provides a array manufacturing apparatus for manufacturing a array by dispensing on a substrate a minute volume of the liquid including probes capable of being connected for a target substance in the peculiarity comprising: a liquid holding member for holding the liquid therein, and capable of dispensing the liquid from a dispensing vent provided at one end thereof; and a driving member for moving the liquid holding member before and after along the dispensing direction; whereby the liquid held to the liquid holding member is dispensed by moving the liquid holding member with the driving means; and further comprising a relative moving member which relatively moves the substrate and the liquid holding member in a plane orthogonal to the dispensing direction of the liquid In the present invention, the liquid supplied to the liquid holding member is accommodated, is formed in such a manner that the liquid surface is opened so as to contact it to atmosphere directly, the liquid holding member has an other side which is made an opening end at opposite side to the dispense vent, the opening end is formed so as to soak it in the liquid in the liquid container, and the liquid is supplied in the liquid holding member from the liquid container under the capillary action.

In addition, the above invention, the relative moving means is constructed in such a manner that the relative position of the substrate and the conduit member is changed by moving the substrate.

According to the present invention, there is provided an array manufacturing apparatus for manufacturing a micro array by dispensing on a substrate a minute volume of the liquid including probes capable of being connected for a target substance in the peculiarity comprising: a liquid holding member for holding the liquid therein, and having a dispense vent for dispensing the liquid at one end and having an opening end provided at another end, a driving member for generating dispense pressure to dispense the liquid held to the liquid holding member, a relative moving member for relatively moving the substrate and the liquid holding member in a plane orthogonal to the dispensing direction of the liquid, and a liquid container for accommodating the liquid supplied to the liquid holding member and is formed in such a manner that the liquid surface is opened so as to contact it to atmosphere directly, whereby the opening end of the liquid holding member being made soaked into the liquid in the liquid container, and the liquid is supplied in the liquid holding member from the liquid container under the capillary phenomenon. and the liquid is supplied in the liquid holding member from the liquid container under the capillary action.

According to other aspect of the present invention, the driving member is made a member for adding thermal energy to the liquid held in the liquid holding member.

According to the present invention, the driving member is made a member for deforming an internal shape of the liquid holding member.

In the above invention, the liquid including the probe capable of being combined to the target materials in peculiarity, is held to the internal conduit, and The conduit member having the dispense vent at the one end of the conduit is moved before and after by the driving means along the dispensing direction, so that when the conduit member, which moves in a direction advanced according to the dispensing direction, is stopped, Inertia force acts on the liquid in the conduit member, and the flow facing the dispensing direction is generated in the liquid in the conduit, and then the liquid drop of a minute volume is dispensed on the substrate from the dispense vent by the flow. By repeating the dispense of the liquid drop of such a minute volume, while changing a relative position of the substrate and the conduit member in a plane orthogonal to the dispensing direction by the relative moving means, the liquid is dispensed to the desired position on the substrate and thus the micro array is manufactured.

According to the above invention, even if the inertia force acting on the liquid is a case that the bubble exists in the conduit, the size thereof does not change, so that irrespective of presence of the bubble, the liquid of a constant volume can be dispensed with the constant rate. Therefore, the volume of the dispense of the liquid dispensing on the substrate and the precision at the dispense position can be improved.

Moreover, the conduit member holds the liquid to the internal conduit, and thus the pressure supplied to the liquid by the conduit member's movement rises in the dispense vent neighborhood, so that the dispense speed of the liquid can be made large.

In the above invention, the another edge of the conduit having the dispense vent to one end provided in the conduit member becomes an opened end, a liquid container of the opened end to supply the liquid which includes the probe capable of being combined to the target in the peculiarity to the conduit member, and the liquid container is constituted that it soaked in the liquid in the accommodated liquid container so that liquid level was opened to atmosphere, so that the liquid is supplied by the capillary phenomenon by the liquid container in the conduit member and thus the liquid is held in the internal conduit. By movement in the conduit member by the driving means according to the dispensing direction, when the conduit member moved in a direction advanced along the dispensing direction, stops, inertia force acts on the liquid in the conduit member, and the flow facing the dispensing direction is generated in the liquid in the conduit, and thus the liquid drop of a minute volume is dispensed on the substrate from the dispense vent by the flow. By repeating the dispense of the liquid drop of such a minute volume, while changing a relative position of the substrate and the conduit member in a plane orthogonal to the dispensing direction by the relative moving means, the liquid is dispensed to the desired position on the substrate and thus the array is manufactured.

According to the above invention, even if the inertia force acting on the liquid is a case that the bubble exists in the conduit, and the size thereof does not change, so that irrespective of the presence of the bubble, the liquid of a constant volume may be dispensed with the constant rate. Therefore, the dispense volume of the liquid dispensing on the substrate and the precision at the dispense position, can be improved.

Moreover, the conduit member holds the liquid to the internal conduit, and thus the pressure supplied to the liquid by the conduit member's movement rises in the dispense vent neighborhood, so that the dispense speed of the liquid can be made large.

In addition, the liquid supply mechanism to introduce the liquid into the conduit in the conduit member becomes unnecessary, so that the downsizing of the apparatus and the decrease of the apparatus cost become possible.

According to the above invention, when a relative position of the substrate and the conduit member is changed by the relative displacement means, the substrate is moved, but the conduit member is not moved, so that even if a relative position is changed, the meniscus position of the dispense vent of the conduit member does not displaced as a result of this, precision of dispense position of the liquid does not become worse.

BRIEF DESCRIPTION OF THE DRAWINGS

FIG. 16 is an explanatory view showing the liquid pipette means having the slit with the swelling on the way according to the embodiment of the present invention;

FIG. 17 is an explanatory view showing the liquid pipette means having the needle member at the tip of a straight recess according to the embodiment of the present invention;

FIG. 30 is a schematic diagram showing the liquid dispense apparatus according to the sixth embodiment of the present invention;

FIGS. 31(a)–(j) are enlarged views showing the liquid dispense means according to the sixth embodiment of the present invention;

SUITABLE EMBODIMENT OF INVENTION

Hereafter, embodiments of the present invention are explained with reference to the drawings. Moreover, common numeral references are made to a common portion through the drawings.

First Embodiment (Construction)

Figure 1:
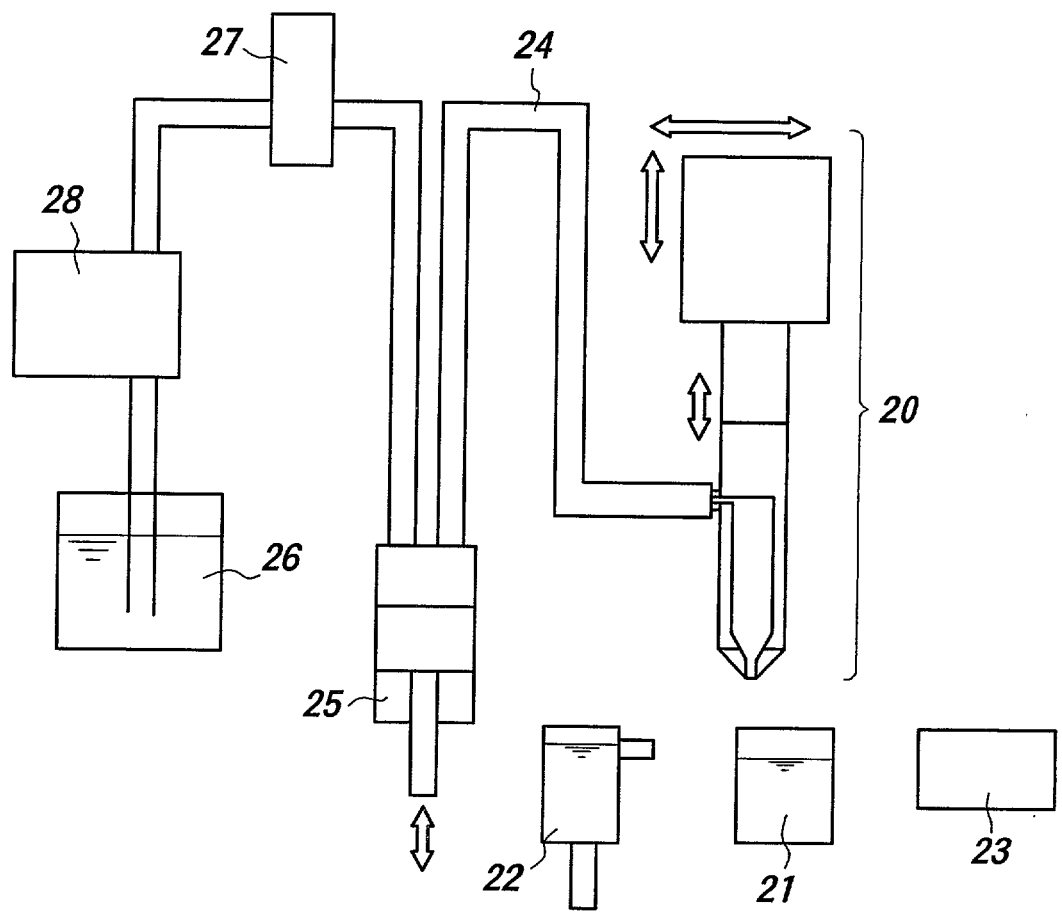
FIG. 1 is a schematic block diagram showing the main portion of the liquid pipetting apparatus according to the first embodiment of the present invention, by a cross-section.
Figure 2:
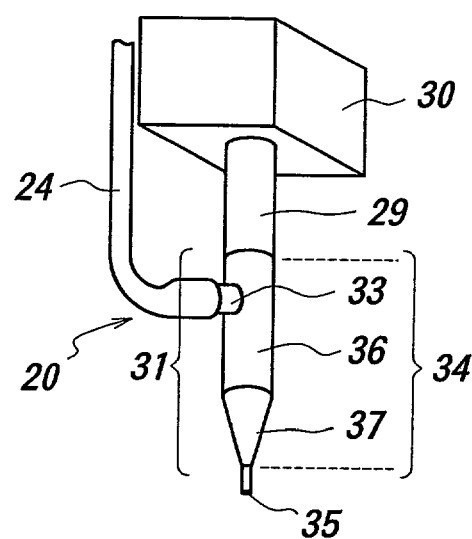
FIG. 2 is a perspective view of the liquid dispense means according to the embodiment of the present invention.
Figure 3:
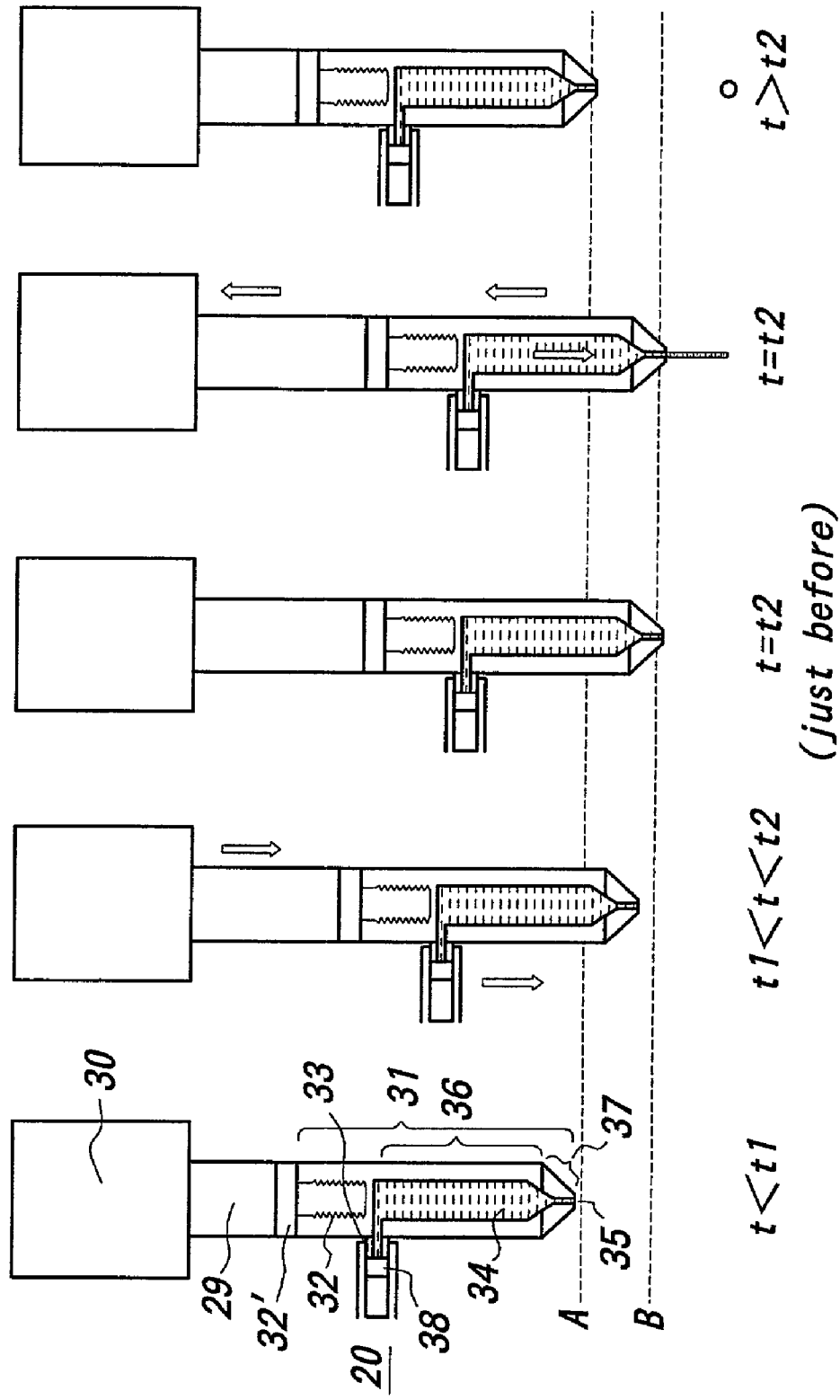
FIG. 3 is a cross-sectional view showing the dispense operation of the liquid dispense means according to the embodiment of the present invention.
Figure 4:
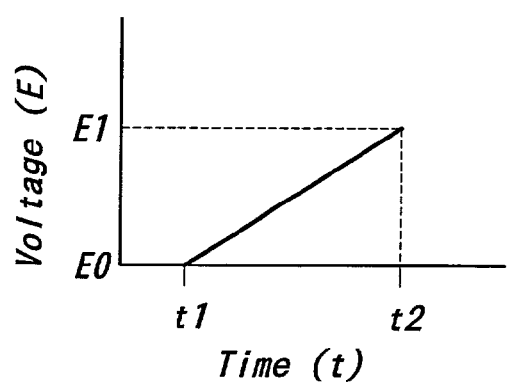
FIG. 4 is a driving voltage wave form chart of the laminated piezo-electric element according to the embodiment of the present invention.

First embodiment of the present invention is shown in FIGS. 1 to 4. FIG. 1 is a schematic diagram showing the liquid pipetting apparatus of the first embodiment; FIG. 2 is a perspective view of the liquid dispense means; FIG. 3 is a cross-sectional view showing the dispense operation of the liquid dispense means; and FIG. 4 shows a driving voltage wave form of the laminated piezo-electric element.

In the FIG. 1, a liquid dispense means 20 is supported on the movable transportation member (not shown), and is arranged so as to move over an inspection specimen container 21, a washing tank 22, and a reactive container 23, respectively. One end of the liquid dispense means 20 is connected to a syringe piston pump 25 through a piping 24 made of Teflon (Trade name). In addition to the connecting piping 24, the syringe piston pump 25 is further connected to another piping, which is connected to a liquid supply tank 26 through a solenoid valve 27 and a conveying pump 28.

The piston of the above-mentioned syringe piston pump 25 reciprocates by a linear shuttling actuator such as stepping motors and the gear rack and pinions (not shown) in the direction of the arrow. Moreover, the liquid dispense means 20, the syringe piston pump 25 and the liquid service tank 26 are arranged at substantially same leveling position. The water being washing water or the degassed ion exchange water enters in the liquid supplying tank 26, and thus the washing water is filled and supplied to the respective piping 24, the syringe piston pump 25, and the liquid dispense means 20 by the conveying pump 28.

As described later, the liquid pipetting apparatus of the FIG. 1 sucks the inspection sample from the inspection specimen container 21, and is dispensed to the reactive container 23 afterwards. Hundreds of kinds of and several thousands of kinds of handled liquid samples are present in a blood test machine and a pharmaceutical inspection, so that in the method of dispensing the liquid filled to the reservoir as in the ink jet printer, many steps are required to the exchange work of the liquid in the reservoir, and as to the inspection sample which can gather only a small volume as in the infant specimen, there is a problem that the conduit between the reservoir and the nozzle cannot be filled. Therefore, it is thought that the aspirating and dispensing methods are preferable to pipette such various liquid samples.

Next, the constitution of the liquid dispense means 20 is explained with reference to FIGS. 2, 3 and 4. The liquid dispense means 20 uses a laminated piezo-electric element 29 as an acceleration applying element. The one end of the laminated piezoelectric element 29 is secured to a trestle 30, and another edge is secured to a conduit member 31. The conduit member 31 is constituted from a liquid introducing vent 33, a conduit 34 and a nozzle 35. The liquid introducing vent 33 is connected to the syringe piston pump 25 through the Teflon piping 24. The conduit 34 is formed by a straight portion 36 and a taper portion 37, and sizes of the straight portion 36 are a diameter of φ 0.5 mm–φ 4 mm, and a length of 2 mm–15 mm. Moreover, the taper portion 37 is formed from the straight portion 36 toward nozzle 35, and the cone angle is 10–45 degrees. The nozzle 35 has a diameter of φ 0.03 mm–φ 0.15 mm and a length of 0.05 mm–1 mm. The water repellent layer according to fluororesin being a low surface energy substance (not shown in the figure by the sign) is provided to the end face and the outer periphery of the nozzle 35. The connection between the laminated piezo-electric element 29 and the conduit 34 is formed as a rigid body, so that the volume of the conduit 34 does not change by the displacement of the laminated piezo-electric element 29. Moreover, one end of the laminated piezo-electric element 29 is secured to the trestle 30, so that the whole of conduit member 31 is displaced vertically on the drawing along with the displacement of the laminated piezo-electric element 29. The voltage of the desired wave form is supplied from the driving circuit (not shown) to the laminated piezo-electric element 29 by a lead wire or a flexible substrate.

(Function)

The liquid dispense means 20 is moved over the washing tank 22, the nozzle 35 of liquid dispense means 20 is soaked in the washing tank 22 by 1 mm–2 mm, the electromagnetic valve 27 is opened, The washing water in the liquid supply tank 26 is sent by the water supply pump 28, and the inner periphery surface of the conduit 34, the outer peripheral surfaces and end surfaces of nozzle 35 are washed by the washing water. During the sending of the washing water, the syringe piston pump 25 moves to the middle point, and the washing water is filled in the syringe piston pump 25. Afterwards, the solenoid valve 27 is shut, and the liquid dispense means 20 rises again up over the washing tank 22.

After this, the piston of the syringe piston pump 25 moves upward by a given volume, and the washing water is dispensed from the nozzle 35. Afterwards, the piston of the syringe piston pump 25 moves to the middle point again, and the air of a given volume is drawn in the conduit 34. Next, the liquid dispense means 20 moves over the inspection specimen container 21, and the nozzle 35 is soaked in the inspection sample of the inspection specimen container 21. After this, the piston of the syringe piston pump 25 moves in the lower direction by given volume, and the inspection sample is aspirated from the nozzle 35. At this time, the washing water and the inspection sample in the piping 24 and the conduit 34 are separated by air layer 38.

Then, the liquid dispense means 20 rises again up over the inspection specimen container 21. At this time, the water repellent layer of fluororesin is formed on the end face and the outer peripheral surface of the nozzle 35, so that the inspection sample does not adhere to the end faces and outer peripheral surfaces of the nozzle 35. Afterwards, the liquid dispense means 20 is moved over the reactive container 23, and the inspection sample is dispensed to the reactive container 23.

Next, the dispensing operation is explained with reference to FIGS. 3 and 4. In the initial state of instant t<t1 and E0 in FIG. 3(*a*), the voltage liquid dispense means 20 is in rest state. The position of nozzle 35 at this time is assumed to be A in FIG. 3. During instants t1<t<t2 of FIG. 3(*b*), the voltage rises gradually, therefore, the liquid dispense means 20 is slowly displaced downward on the drawing. Just before instant t=t2 of FIG. 3(*c*), the displacement corresponding to the voltage E1 is caused in the laminated piezo-electric element 29, the nozzle 35 descends to the position of B. In addition, in instant t=t2 of FIG. 3(*d*), the voltage instantaneously decreases to the voltage E0, and thus the liquid dispense means 20 also displaces upward rapidly as the decrease of the voltage. At this time, inertia force acts downward on the drawing in the inspection sample in the conduit 34, and thus a relative flow generates in the conduit 34. The pressure of the inspection sample in the taper portion 37 rises by this flow, and the inspection sample is dispensing from nozzle 35. The volume of the dispensing liquid is different according to the aperture of the nozzle 35, the value of physical properties of the inspection sample, and driving voltage wave form or the like but it is about 0.01 nl–0.3 μL. After this, the liquid dispense means 20 returns to an initial position in the instant t>t2 of FIG. 3(*e*).

Then, the operation of FIGS. 3(*a*)–(*e*) is repeated, the inspection sample of the given volume is dispensed to the reactive container 23.

In the case of the hemanalysis machine, the dispense volume of the inspection sample is different with the analysis items. For example, in the case that the dispense volume of 0.5 μL is necessary, the dispense volume of one time is made 0.1 μL by adjusting the driving voltage wave form, five drops of the dispense volume may be dispensed as the reactive container. Moreover, in the case that a large dispense volume of 1 μL or more is required, the syringe piston pump 25 should be driven in synchronization with the liquid dispense means 20. That is, since the pipe line consisting of the conduit 34 and the piping 24 is a closed system, when a large volume of the inspection sample is dispensed continuously, the negative pressure in the piping becomes large, therefore, the meniscus of the nozzle 35 retreats backward and the dispense volume decreases. In the case that the dispense volume becomes 1 μL or less the volume of the retreat of the meniscus can be little, and disregarded, but when the dispense volume exceeds 1 μL, the volume of the retreat of the meniscus becomes large to the extent which cannot be disregarded, and thus the desired dispensing volume might not be obtained. To prevent this, when the volume of 1 μL or more is dispensed, every time the liquid of 1 μL is dispensed, the volume of the pipe line is decreased by 1 μL, with the syringe piston pump 25, and the negative pressure in the piping should be recovered to about the atmospheric pressure.

(Effect)

As for this embodiment, since the acceleration applying element does not touch the inspection sample directly, the improvement of washing of the conduit becomes possible. In addition, the partition element such as diaphragms is not used, so that the decrease of the cost becomes possible. Additionally, instead of effecting the acceleration on the liquid by decreasing the conduit volume as in the prior art, the whole of conduit member 31 is rapidly displaced, inertia force is made to act on the inspection sample held to conduit 34 and the sample is dispensing, so that the inertia force act on the inspection sample held to conduit 34 and since it is dispensed even if the bubble exists in the conduit 34, the inspection sample can be dispensed. In addition, the liquid is dispensed with non-contact from the dispense vent having a small area, so that the liquid of a small volume can be dispensed with high accuracy.

Moreover, in the present embodiment, the laminated piezoelectric element 29 was used as an acceleration applying element, but this acceleration applying element is not limited to this, if there is an actuator capable of performing the reciprocation action causing a relative flow, similar function and the effect can be achieved with. For example, an air cylinder, a solenoid or magnet-strictive actuator and a piezo-electric bimorph can be used, and also, the mechanism converting rotary motion into rectilinear motion such as rack pinions and the motor such as pulse motors may be combined.

Figure 5:
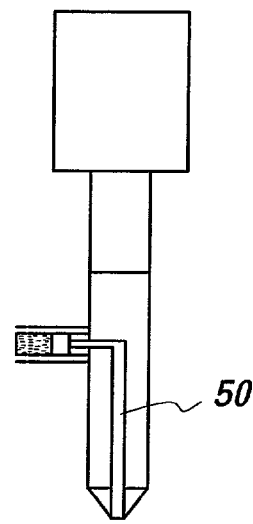
FIG. 5 is a partially cross-sectional side view showing the liquid pipetting means with the conduit of a straight shape according to the embodiment of the present invention.
Figure 6:
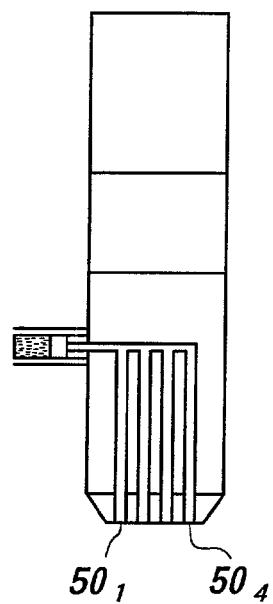
FIG. 6 is a partly sectional side view showing the liquid pipetting apparatus to have the channel which has diverged to the plural channels on the way according to the embodiment of the present invention.

Moreover, in the present embodiment, the conduit 34 consisting of the straight portion 36 and the taper portion 37 is used, but the conduit 34 is not limited to this, For example, a straight shaped conduit 50 having the same cross-sectional area as the nozzle 35 as in FIG. 5 can be used. The dispense operation in such straight shaped conduit 50 is performed by rapidly stopping conduit member 45 which moves to the dispensing direction or by reversing the direction of the movement. By this operation, the liquid is dispensed by the generation of the flow going to the dispensing direction. Therefore, in addition to the same effect as the above described embodiment, the steps required for making the liquid because of simple conduit shape can be reduced. Furthermore, as in FIG. 6, a similar effect can be obtained even by the member which has diverged to the plural conduit on the way.

Moreover, the liquid introducing vent 33 in the present embodiment is provided to the dispensing direction and horizontally, but a similar effect is achieved even if the vent 33 is installed in the same direction as the liquid dispensing direction.

Figure 7:
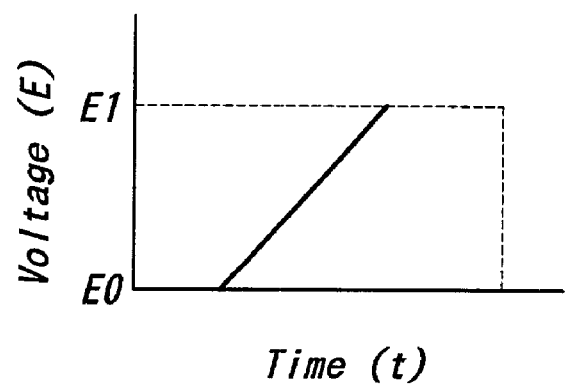
FIG. 7 is a voltage wave form chart showing the wave shape, in which after increasing up to the voltage E1 according to the embodiment of the present invention, the voltage is maintained for a certain time, and is decreased rapidly afterwards.
Figure 20:
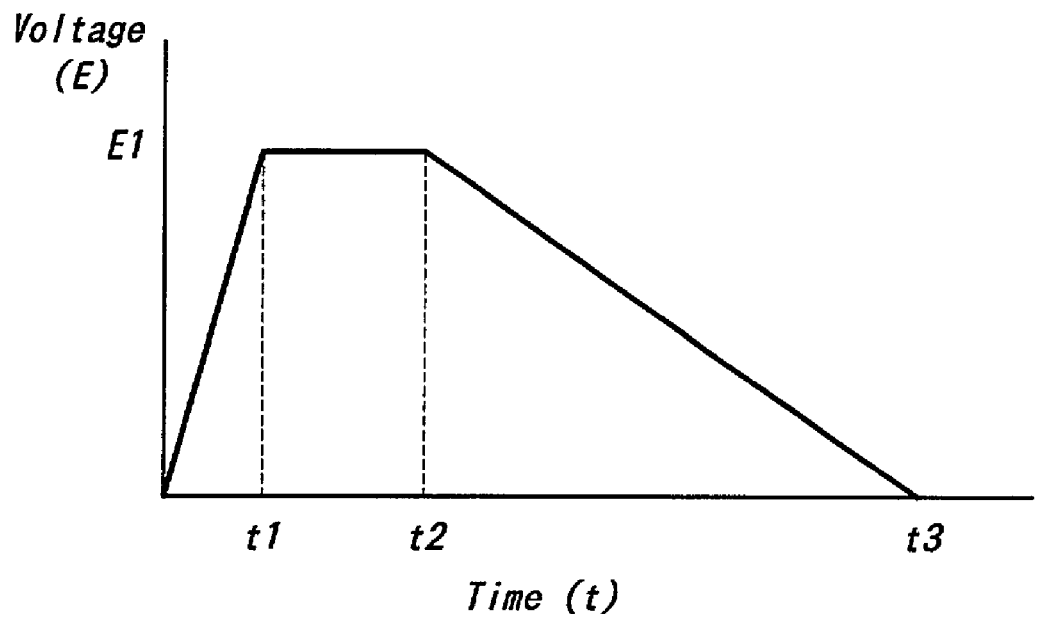
FIG. 20 is a wave form chart showing the wave form in which after applying the voltage E1, it maintains during the instants t1–t2, afterwards the voltage E1 is decreased gradually, according to the embodiment of the present invention.
Figure 21:
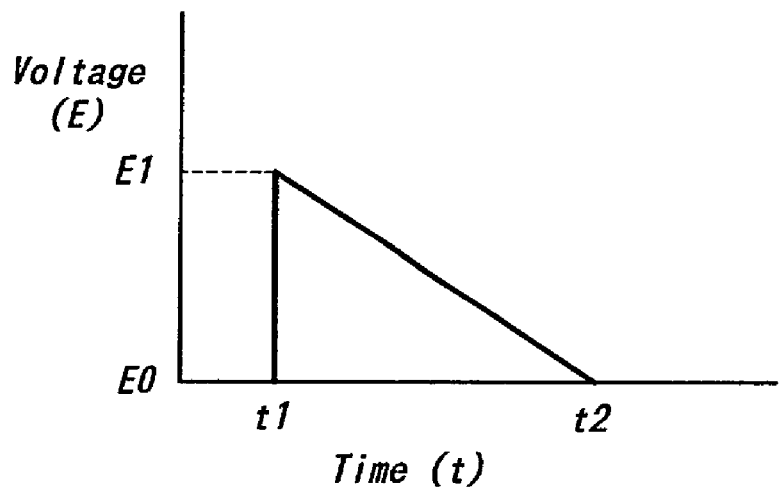
FIG. 21 is a wave form chart showing the driving voltage wave form of the laminated piezo-electric element in the first modification of the third embodiment, according to the embodiment of the present invention.

Moreover, the voltage wave form for driving the laminated piezo-electric elements is not limited to the wave form of FIG. 4, for example, as in FIG. 7, after maintaining certain time with the voltage rised up to the voltage E1, voltage wave form rapidly decreased and as shown in FIG. 20, voltage E1 is rapidly supplied between instants t0–t1, and this voltage E1 is held between instants t1–t2, afterwards, the shape of waves decreasing gradually, may be used. The dispense operation of the shape of waves in FIG. 21 is performed as follows. First of all, the liquid dispensing means 20 moves between instants t0–t1 downward. The inspection sample held to conduit 34 moves downward along with the movement of the liquid dispense means 20 since the conduit 34 and the piping 24 communicated thereto, are shut with the solenoid valve 27. Afterwards, the movement of the liquid dispense means stops when it reaches instant t1. At this time, inertia force acts on the inspection sample in conduit 34 downward, and the inspection sample is dispensed from the nozzle 35 by the inertia force. Afterwards, the liquid dispense means 20 returns to an initial position by the voltage gradually decreasing between instants t2–t3. Thus, a similar effect as the above described embodiment is achieved in the case of the voltage wave to cause the liquid dispense means 20 and a relative flow in the inspection sample held to the conduit 34.

Second Embodiment (Constitution)

FIGS. 8 to 11 show the second embodiment of the present invention.

Figure 8:
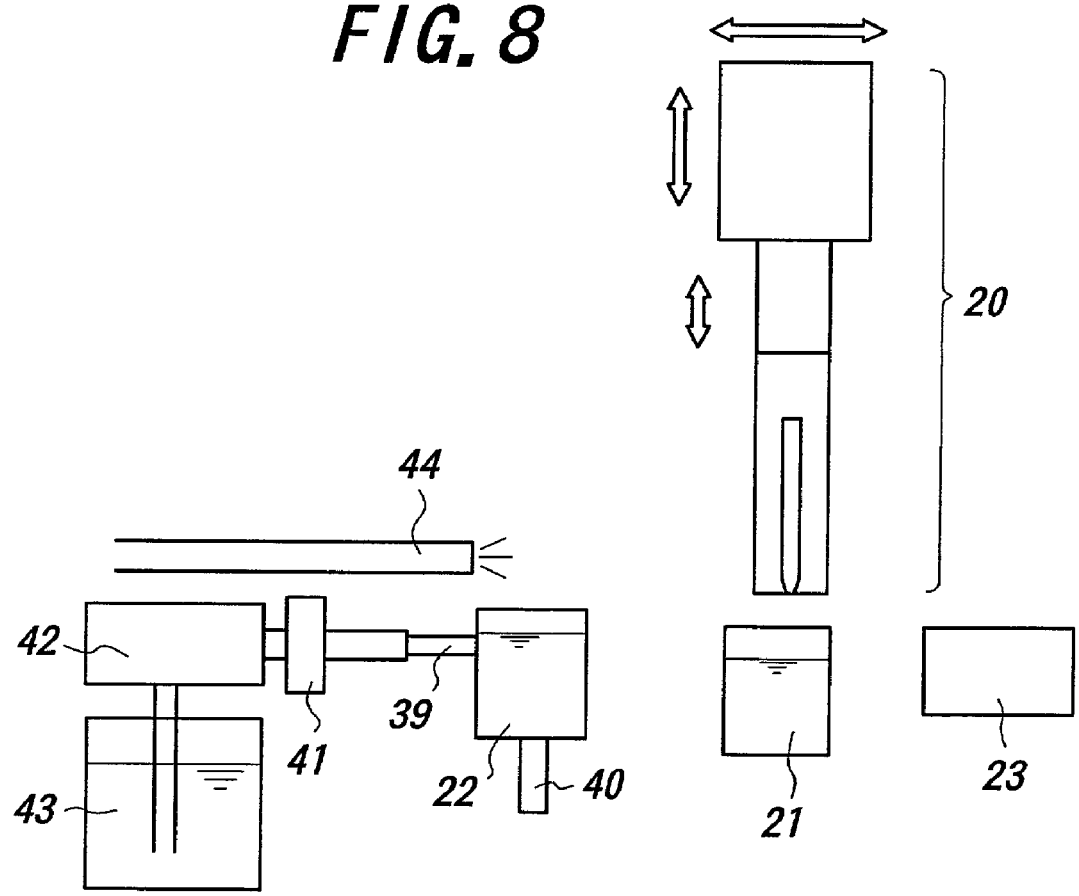
FIG. 8 is a schematic diagram of the liquid pipetting apparatus according to the second embodiment of the present invention.
Figure 9:
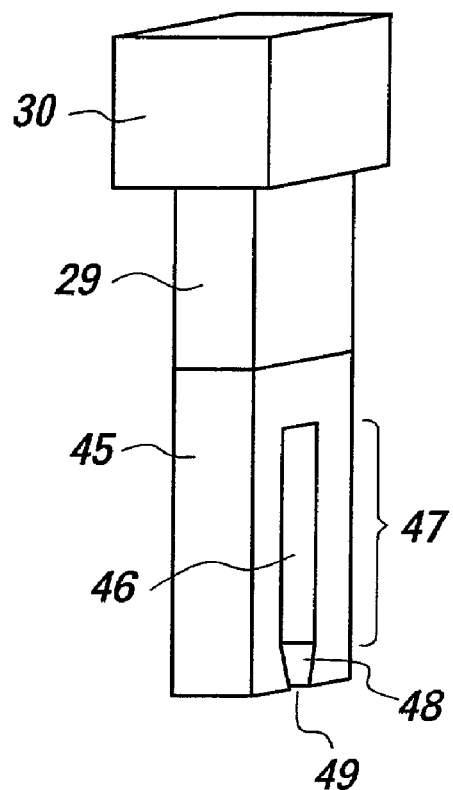
FIG. 9 is a perspective view showing the liquid dispense means according to the embodiment of the present invention.
Figure 10:
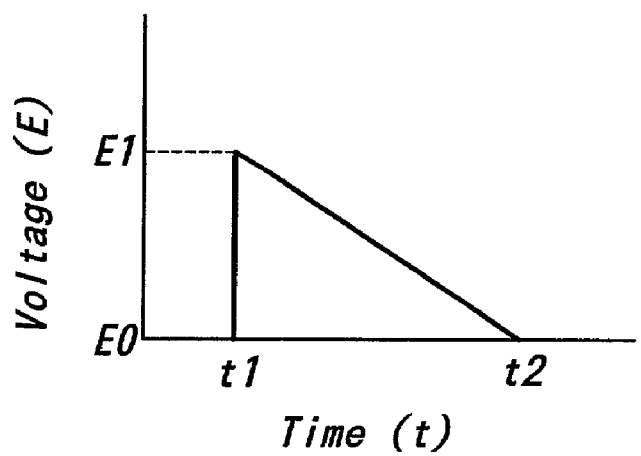
FIG. 10 is a wave form chart showing the driving voltage wave form of the laminated piezo-electric element according to the embodiment of the present invention.
Figure 11:
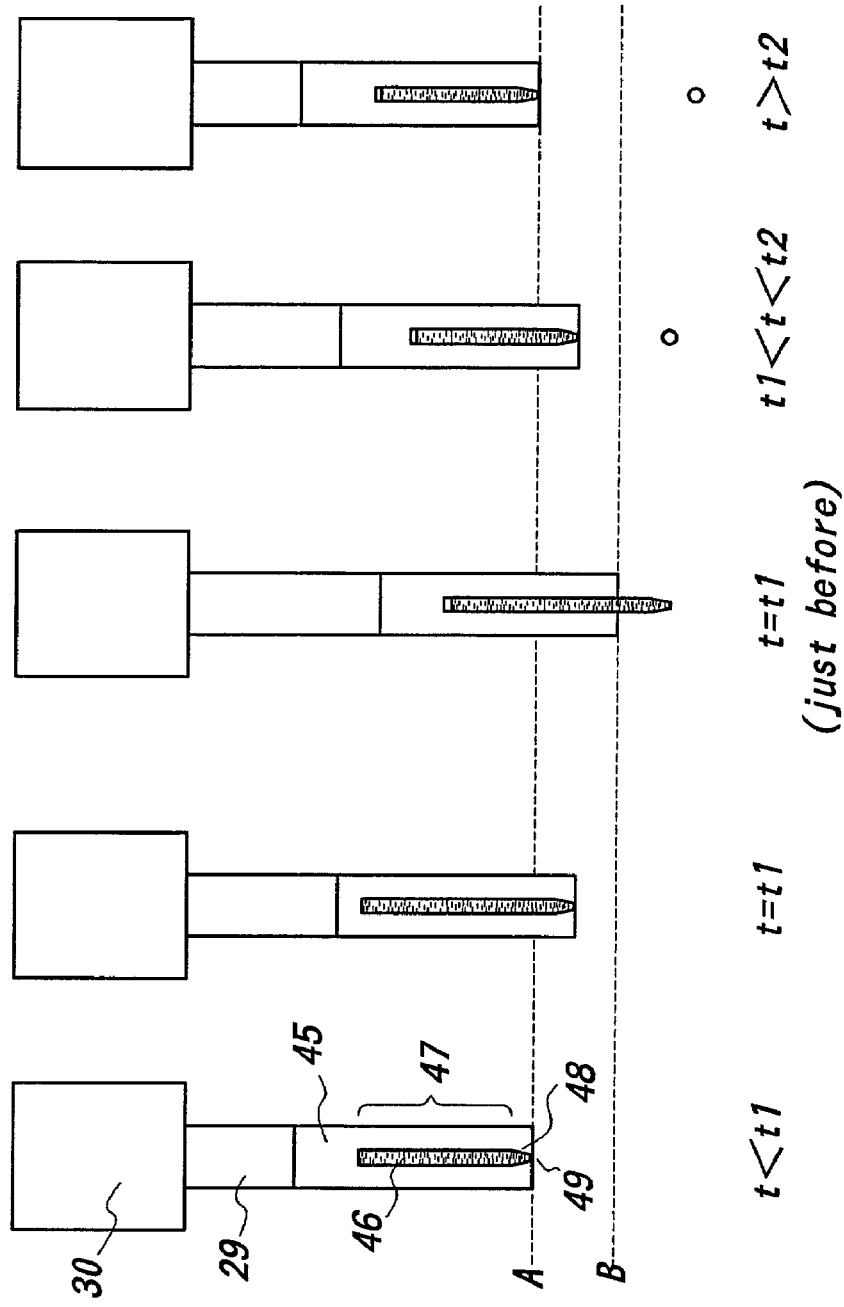
FIGS. 11(a)–(e) are explanatory views showing the operation of the liquid dispense means according to the embodiment of the present invention.

FIG. 8 is a schematic diagram of the liquid pipetting apparatus, FIG. 9 is a perspective view of liquid dispense means 20, FIG. 10 is a driving voltage wave chart of the laminated piezo-electric element and FIG. 11 shows the operation of the liquid dispense means 20.

In FIG. 8, the liquid dispense means 20 is supported to the movable transportation member (not shown), and is movably arranged over the inspection specimen container 21, the washing tank 22 and the reactive container 23, respectively.

The introducing vent 39 and an outlet 40 are provided to the washing tank 22, the introducing vent 39 is connected to a solenoid valve 41, a conveying pump 42, and a washing water tank 43 one by one through the Teflon piping. The outlet 40 is connected to the waste fluid container (not shown) through the Teflon piping.

Moreover, an air injection vent 44 has been provided over the washing tank 22. An air supply means (not shown) is connected to the air injection vent 44, thereby gushing the air.

As shown in FIG. 9, the liquid dispense means 20 consists of a laminated piezo-electric element 29 and a liquid supporting member 45. The one end of the laminated piezo-electric element 29 is secured to the trestle 30 supported on the movable transportation member (not shown), and the other end thereof is connected to the liquid supporting member 45. The liquid supporting member 45 have a recess portion 46 of a small cross-sectional area, and thus the water repellent layer of the fluorine system resin being the low surface energy substance is provided to the surfaces except of the recess portion 46. Moreover, the recess portion 46 constitutes of the straight portion 47, the taper portion 48 and the dispense entrance 49.

(Operation)

As shown in FIGS. 8 and 9, the liquid dispense means 20 is moved over the washing tank 22, and the liquid supporting member 45 are made to intrude in the washing tank 22. Next, the solenoid valve 41 is opened and the washing water is supplied to the washing tank 22 by the conveying pump 42 and the liquid supporting member 45 is washed. Subsequent, the air is sprayed from the air exhaust nozzle 44 on recess portion 46 of fluid supporting member 45, and the liquid dispense means 20 is moved upward from the washing layer 22, while removing the washing water held to the recess portion 46. Next, the liquid dispense means 20 is moved over the inspection specimen container 21, The tip portion of the liquid supporting member 45 is soaked in the inspection sample of the inspection specimen container 21 by 1 mm–2 mm. The inspection sample is aspirated up by the surface tension of the recess portion 46, and a given volume of the inspection sample is held to the recess portion 46. At this time, the water repellent layer of a fluorine system resin is formed on the outer periphery plane of the liquid supporting member 45, the inspection sample does not adhere to the outer periphery plane of the liquid supporting member 45.

After this, the liquid dispense means 20 is moved over the reactive container 23, and then the inspection sample is charged. The dispense of the inspection sample is performed as shown in FIG. 11. The liquid dispense means 20 is in the initial rest state at the instant t<t1 of FIG. 11($a$). When the voltage E=E1 is applied at instant t=t1 of FIG. 11($b$), the liquid dispense means 20 is displaced from level A to level B. Immediately after the instant t=t1 of FIG. 11($c$), the direction of the displacement of liquid dispense means 20 reverses downward direction to upward direction, at this time, the inertia force acts on the inspection sample held to the recess portion 46, A relative flow is generated downward on the drawing, and is dispensed from the dispense vent 49. After this, the voltage decreases from E1 to E0, gradually during instants t1<t<t2 of FIG. 11($d$), the position of the liquid dispense means 20 is displaced from level B to level A, and returns to the initial position at the instant t<t2 of FIG. 10($e$). Then, the operation of FIGS. 11($a$)–11($e$) is repeated, the inspection sample of the given volume is dispensed to the reactive container 21.

(Effect)

In the present embodiment, in addition to the effect of first embodiment, the shape of the liquid holding member 45 is easy, so that number of man-hours required for the manufacture, can be reduced, and thus the decrease of the cost becomes possible. Moreover, the recess portion 46 for holding the inspection sample is opened to external atmosphere, so that washing property becomes excellent.

Moreover, in the present embodiment, the laminated piezo-electric element 29 was used as an acceleration applying element, but this acceleration applying element is not limited to this, if there is an actuator capable of performing the reciprocation action causing a relative flow, similar function and the effect can be achieved with. For example, an air cylinder, a solenoid or magnet-strictive actuator and a piezo-electric bimorph may be used as an acceleration supplying element, and also, the mechanism converting rotary motion into rectilinear motion such as rack pinions and the motor such as pulse motors may be combined.

Figure 12:
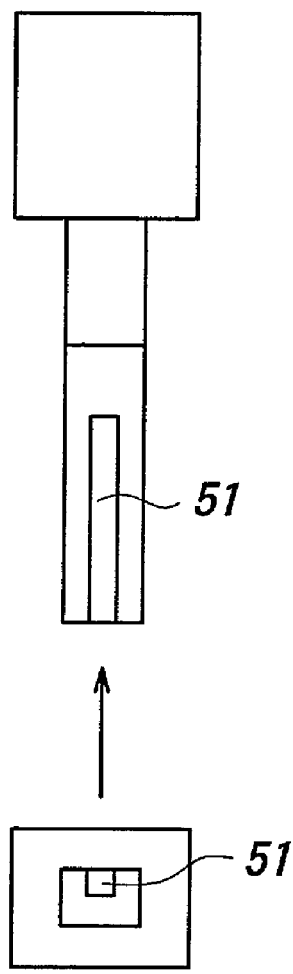
FIG. 12 is an explanatory view showing the liquid pipetting apparatus having the shape of the member by which the liquid of a straight recess according to the embodiment of the present invention is held is had.
Figure 13:
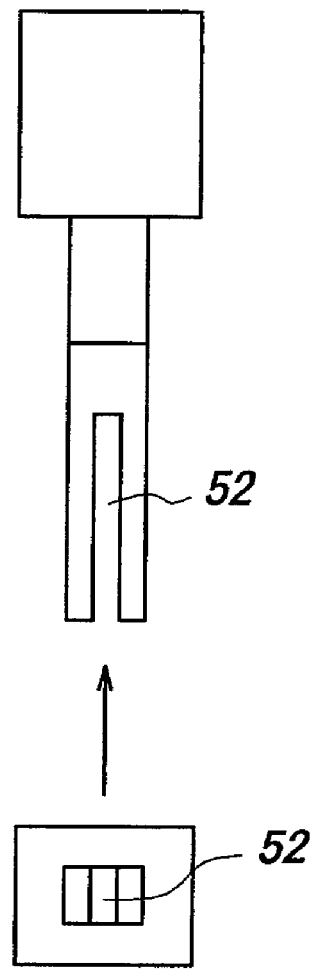
FIG. 13 is an explanatory view showing the liquid pipetting apparatus having the shape of the member by which the liquid of the slit forma according to the embodiment of the present invention is held.
Figure 14:
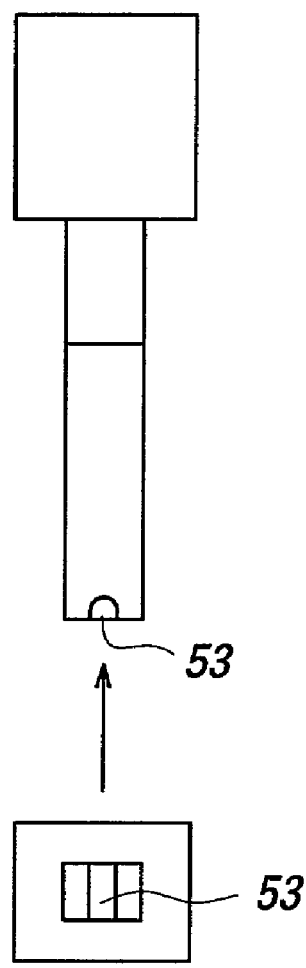
FIG. 14 is an explanatory view showing the liquid pipette means having the member with the notch portion at its tip according to the embodiment of the present invention.
Figure 15:
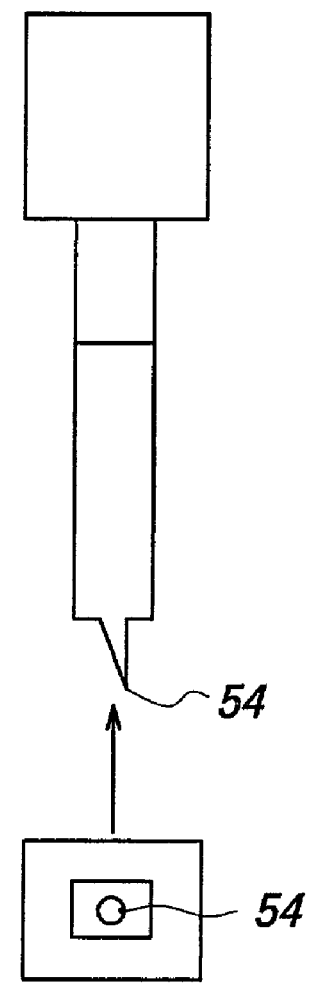
FIG. 15 is an explanatory view showing the liquid pipette means having the needle member according to the embodiment of the present invention.

Moreover, in the present embodiment, the liquid is held by the recess portion 46 consisting of the straight portion 47, the taper portion 48, and the dispense vent 49, but the shape of the member for holding the liquid is not limited to this, for example, a similar effect can be achieved even by a member having a straight recess 51 shown in FIG. 12, a slit 52 shown FIG. 13, and a notch portion 53 at the tip shown in FIG. 14, as well as a needle member 54 shown in FIG. 15. Moreover, even in case of using a slit having swelling 55 on the way as in FIG. 16, and the member or the like, in which the needle member 56 is provided at the tip of straight recess as in FIG. 17, if a relative flow causes in the dispensing direction, a similar effect can be obtained.

Figure 18:
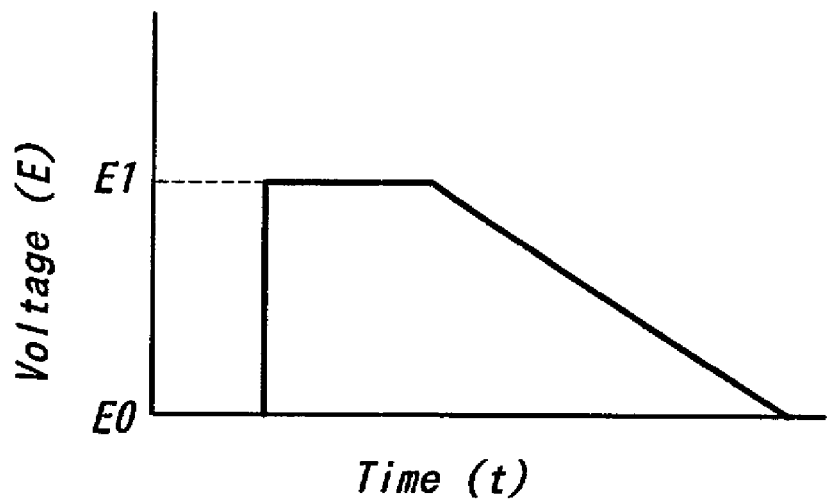
FIG. 18 is a wave form chart showing the wave form that after applying the voltage E1, it maintains a certain time, afterwards decreases gradually, according to the embodiment of the present invention.
Figure 19:
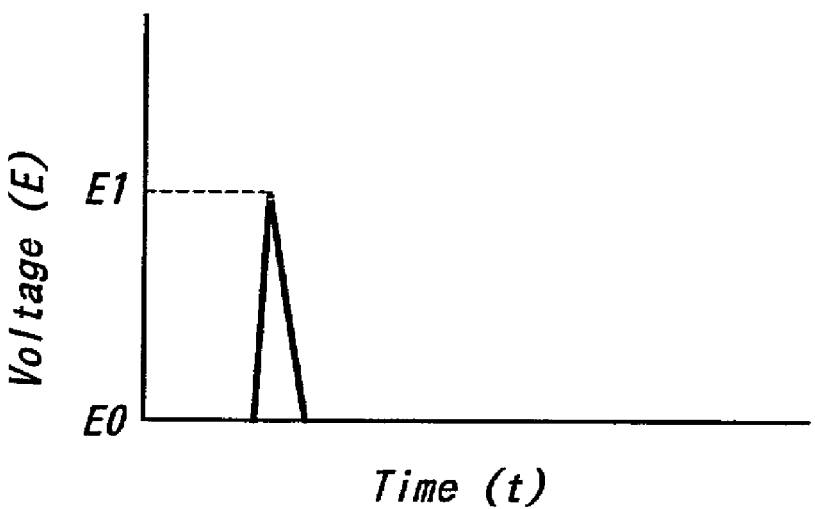
FIG. 19 is a wave form chart showing a triangular wave form according to the embodiment of the present invention.

Moreover, in the present embodiment, the laminated piezoelectric element 29 was driven by the voltage wave form as shown in FIG. 10, but the driving voltage wave form is not limited to this, a similar effect can be obtained, for example, as shown in FIG. 18, even in case of using the wave form, in which the voltage E1 is maintained certain time after applying it, afterwards, decreases gradually, or a triangle wave form as shown in FIG. 19, a similar effect can be obtained.

Third Embodiment (Constitution)

FIGS. 1 to 4 show the third embodiment of the present invention.

FIG. 1 is a schematic diagram showing the dispense apparatus of the first embodiment, FIG. 2 is a perspective view of the liquid dispense means 20, FIG. 3 is across-sectional view showing the change of the state in the dispense operation of the liquid dispense means 20, and FIG. 4 shows a driving voltage form of the laminated piezo-electric element 29.

In the FIG. 1, a liquid dispense means 20 is supported on the movable transportation member (not shown), and is arranged so as to move over an inspection specimen container 21, a washing tank 22, and a reactive container 23, respectively. One end of the liquid dispense means 20 is connected to a syringe piston pump 25 through a piping 24 made of Teflon (Trade name). In addition to the connecting piping 24, the syringe piston pump 25 is further connected to another piping, which is connected to a liquid supply tank 26 through a solenoid valve 27 and a conveying pump 28, one by one by.

The piston of above-mentioned syringe piston pump 25 reciprocates by a linear shuttling actuator such as stepping motors and the gear rack and pinions (not shown) in the direction of arrow. Moreover, the liquid dispense means 20, the syringe piston pump 25 and the liquid supplying tank 26 are arranged at substantially same leveling position.

The water being washing water or the degassed ion exchange water enters in the liquid supplying tank 26, and thus the washing water is filled and supplied to the respective piping 24, the syringe piston pump 25, and the liquid dispense means 20 by the conveying pump 28.

The liquid dispense means 20 uses the laminated piezo-electric element 29 as a driving means. The one end in the direction of the displacement of the laminated piezo-electric element 29 is secured to the trestle, and another edge is secured to a male screw member (32). The male screw member (32) is connected to the conduit member 31 provided on the one end of the conduit member 31, and the conduit member 31 and the laminated piezo-electric element 29 can be detached at the threaded portion thereof.

The conduit member 31 is constituted by the liquid introducing vent 33, the conduit 34 and the nozzle 35. The liquid introducing vent 33 is connected to the syringe piston pump 25 through the Teflon piping 24. The conduit 34 consists of the straight portion 36 and the taper portion 37, and as for its dimension, and as for its schematic size, the straight portion 36 has φ 0.5 mm–φ 4 mm in length and 2 mm–15 mm in diameter. Taper portion 37 is formed toward the nozzle 35 from the straight portion 36, and its tapered angle is 10 degrees–45 degrees. The nozzle 35 has a diameter of φ 0.03 mm–φ 0.15 mm and a length of 0.05 mm–1 mm. The water repellent layer of fluororesin being low surface energy substance is provided to the end face and the outer periphery of the nozzle 35. The portion between the laminated piezo-electric element 29 and the conduit 34 is formed as a rigid body, so that the volume of the conduit 34 does not change by the displacement of the laminated piezo-electric element 29. Moreover, one end of the laminated piezoelectric element 29 is secured to the trestle 30, so that the whole of conduit member 31 is displaced vertically on the drawing along with the displacement of the laminated piezo-electric element 29. The voltage of the desired wave form is supplied from the driving circuit (not shown) to the laminated piezo-electric element 29 by a lead wire or a flexible substrate.

(Function)

First of all, the suck and the dispense operation of the inspection sample are explained.

The liquid dispense means 20 is moved over the washing tank 22, the nozzle 35 of the liquid dispense means 20 is soaked in the washing tank 22 by 1 mm–2 mm, the solenoid valve 27 is opened, water in the liquid service tank 26 is sent to the conduit from the conveying pump 28, and the inner periphery plane of the conduit 34 and the outer periphery plane and the end face of the nozzle 35 are washed by the washing water. During the sending of the washing water, the syringe piston pump 25 moves to the middle point, and the washing water fills the syringe piston pump 25.

Afterwards, the solenoid valve 27 is shut, and the liquid dispense means 20 rises again up over the washing tank 22. After this, the piston of the syringe piston pump 25 moves upward by a given volume, and the washing water is dispensed from the nozzle 35. Afterwards, the piston of the syringe piston pump 25 moves to the middle point again, and the air of the given volume is drawn in the conduit 34, thereby forming the air layer 38.

Next, the liquid dispense means 20 moves over the inspection specimen container 21, and the nozzle 35 is soaked in the inspection sample of the inspection specimen container 21. After this, the piston of the syringe piston pump 25 moves lower direction by given volume, and the inspection sample is aspirated from the nozzle 35, thereby filling the conduit. Therefore, as shown in FIG. 3, the above described air layer 38 is formed in the Teflon piping 24 which is connected to the liquid dispense means 20, thereby separating the washing water and the inspection sample by the air layer.

Then, the liquid dispense means 20 rises again over the inspection specimen container 21. At this time, the water repellent layer of fluororesin is formed on the end face and the outer peripheral surface of the nozzle 35, so that the inspection sample does not adhere to the end faces and outer peripheral surfaces of the nozzle 35. Particularly, at the end face thereof, the liquid can be held only to the conduit in the nozzle 35, thereby forming the meniscus of a constant form. Afterwards, the liquid dispense means 20 is moved over the reactive container 23, and the inspection sample is dispensed to the reactive container 23.

The dispensing operation is explained by using FIG. 3 and 4. The position of the tip of the nozzle 35 in case of instant t<t1 and voltage E=E0 of FIG. 3($a$) is assumed to be the level A. The liquid dispense means 20 is slowly displaced downward on the drawing at instants t1<t<t2 of FIG. 3($b$) along with a gradual rising of the voltage, the expansion corresponding to voltage E1 is caused in the laminated piezo-electric element 29 immediately (or just) before instant t=t2 of FIG. 3($c$), and the tip of the nozzle 35 descends to the position of level B. After this, in the instant t=t2 of FIG. 3($d$), the voltage instantaneously decreases to E0, and thus the liquid dispense means 20 also rapidly displaced upward on the drawing as the voltage decreases. At this time, inertia force acts on the inspection sample in the conduit 34 in the downward direction on the drawing, and the flow is generated in the downward direction on the drawing, thereby dispensing the inspection sample from the nozzle 35. The volume of the dispensing liquid varies according to the nozzle diameter, the value in physical properties of the inspection sample, and the driving voltage wave form or the like, but it is about 0.01 nl–0.3 µl. After this, the liquid dispense means 20 returns to an initial position at instant t>t2 of FIG. 3($e$).

Subsequently, the operations of FIGS. 3($a$)–($e$) are repeated, and the inspection sample of desired volume is dispensed to the reactive container 23.

(Effect)

The present embodiment does not effect of the acceleration on the liquid by decreasing the conduit volume as in the prior art, whole conduit member 31 is rapidly displaced, thereby acting inertia force on the liquid and dispensing it.

Therefore, in the prior art, the actuator and the conduit are connected directly or through the partition such as diaphragms or the like, but in the present embodiment, the conduit 34 and the laminated piezo-electric elements 29 being the driving means are connected through a screw member portion, and thus these member can be formed with the rigid body. Therefore, the laminated piezoelectric element 29 and conduit member 31 can be connected detachably, and the liquid dispensing device which does not change the dispense volume before and behind the detachable working can be provided.

As to the driving voltage waveform of the laminated piezoelectric element of the above third embodiment, three modified embodiments are shown in FIGS. 21–24.

Figure 22:
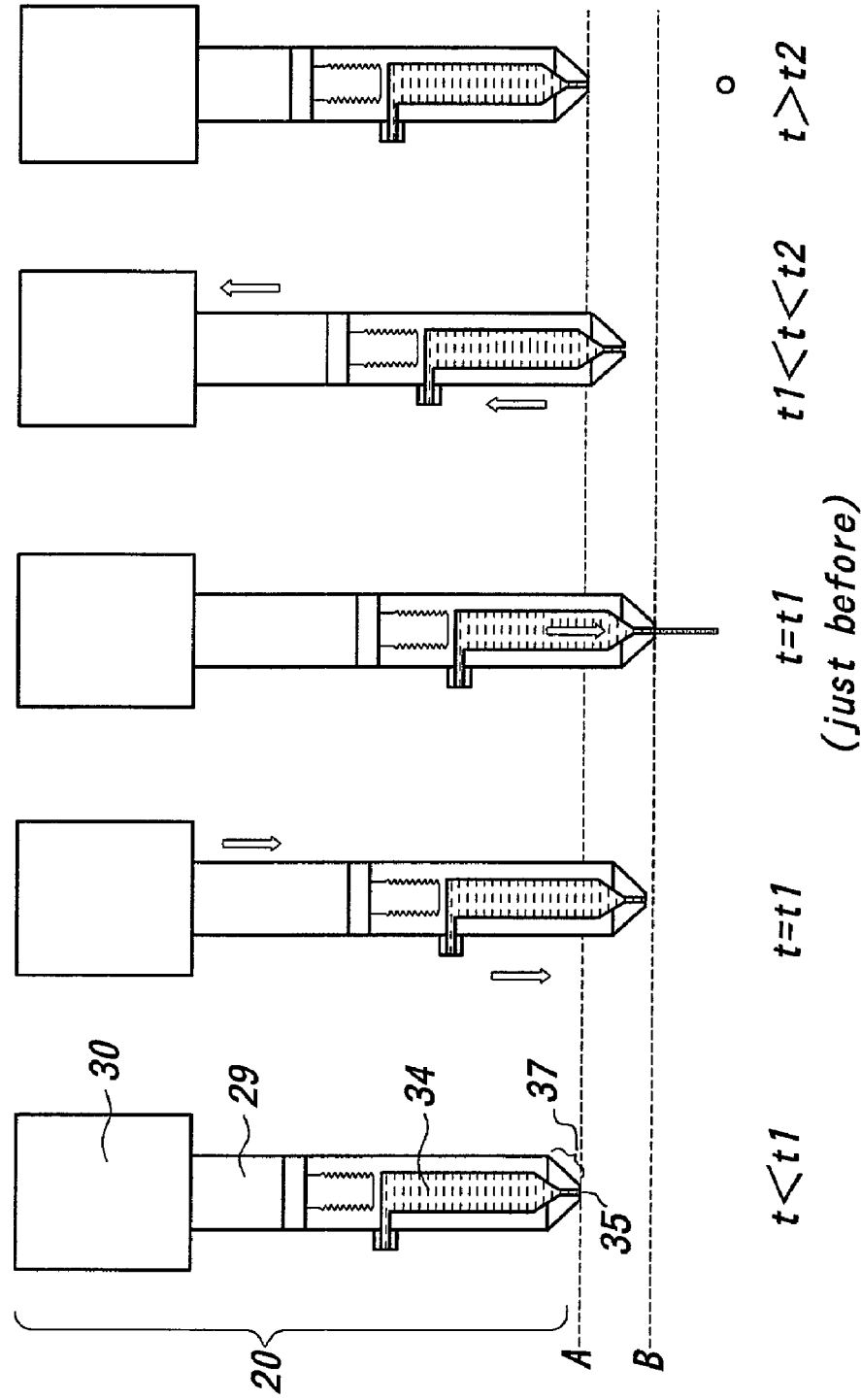
FIGS. 22(a)–(e) are explanatory views showing the dispense operation of the liquid dispense means when driving by the voltage wave form of FIG. 21 according to the third embodiment of the present invention.

FIG. 21 shows the driving voltage wave form of the laminated piezo-electric element in third modified embodiment of the first embodiment, and FIG. 22 shows the dispensing operation of the liquid dispense means 20 in case of driving it with the voltage wave form. In the initial state of the instant t(z)t1 of FIG. 22(a), the liquid dispense means 20 is in rest condition, and when the voltage of E=E1 is supplied at instant t=t1 of FIG. 22(b), the liquid dispense means 20 is displaced downward from level A to level B on the drawing. Immediately after instant t=t1 of FIG. 22(c), the voltage begins to decrease gradually after reaching E1, the displasing direction of the liquid dispense means 20 reverses in accordance with the change in voltage, from upward direction to downward direction on the drawing, too. At this time, inertia force in the downward direction on the drawing acts on the inspection sample in the conduit 34, and the flow thereof is generated toward the nozzle 35, thereby dispensing inspection sample from nozzle 35. During instant t1<t<t2 of FIG. 22(d), the voltage is decreased from E1 to E0 gradually, and according to this, the liquid dispense means is displaced from level B to level A, too. Even during this, the inertia force acts on the inspection sample in conduit 34 in the downward direction on the drawing, however, the acceleration of the liquid dispense means 20 is small, so that the inertia force acting on the inspection sample is also small, and thus the flow thereof is hardly caused. The voltage decreases to E0 at instant t>t2 of FIG. 22(e), the liquid dispense means 20 returns to an initial position, too. Subsequently, the operations of FIGS. 22(a)–(e) are repeated, and the inspection sample of desired volume is dispensed to the reactive container 23.

In the first modified embodiment, the same effect as the first embodiment can be achieved. In addition, in the first embodiment, the inspection sample is dispensed at instant t=t2, but in the first modified, the inspection sample is dispensed at instant t=t1, so that the vibration of the meniscus of the nozzle 35 is early converged and the following inspection sample can be dispensed at short intervals of time.

Figure 23:
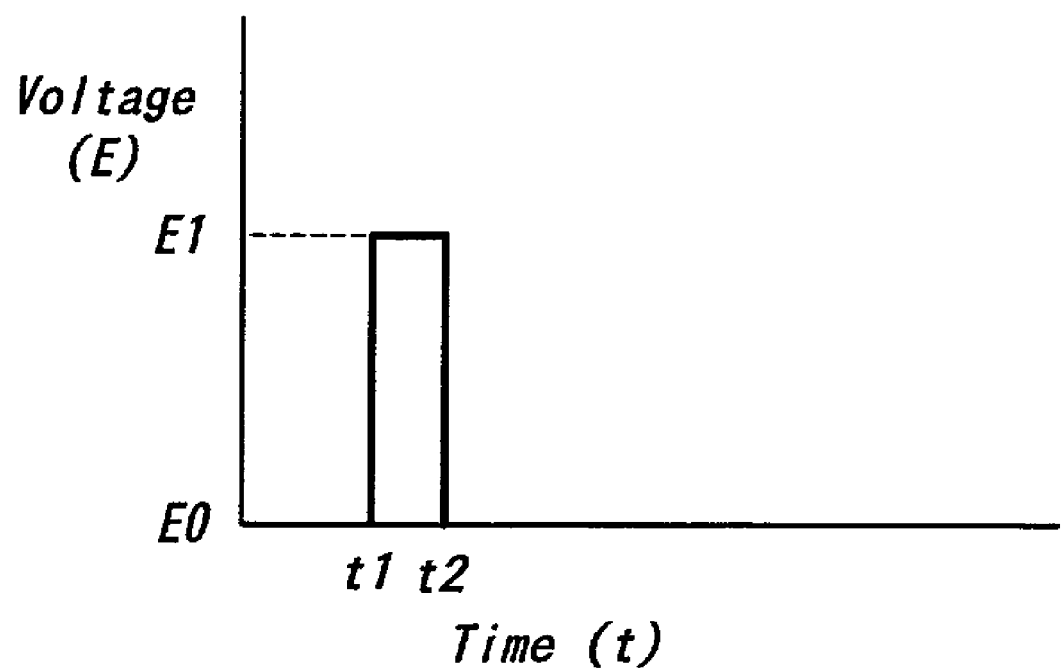
FIG. 23 is a wave form chart showing a driving voltage wave form of the laminated piezo-electric element in the second modification of the third embodiment of the present invention.
Figure 24:
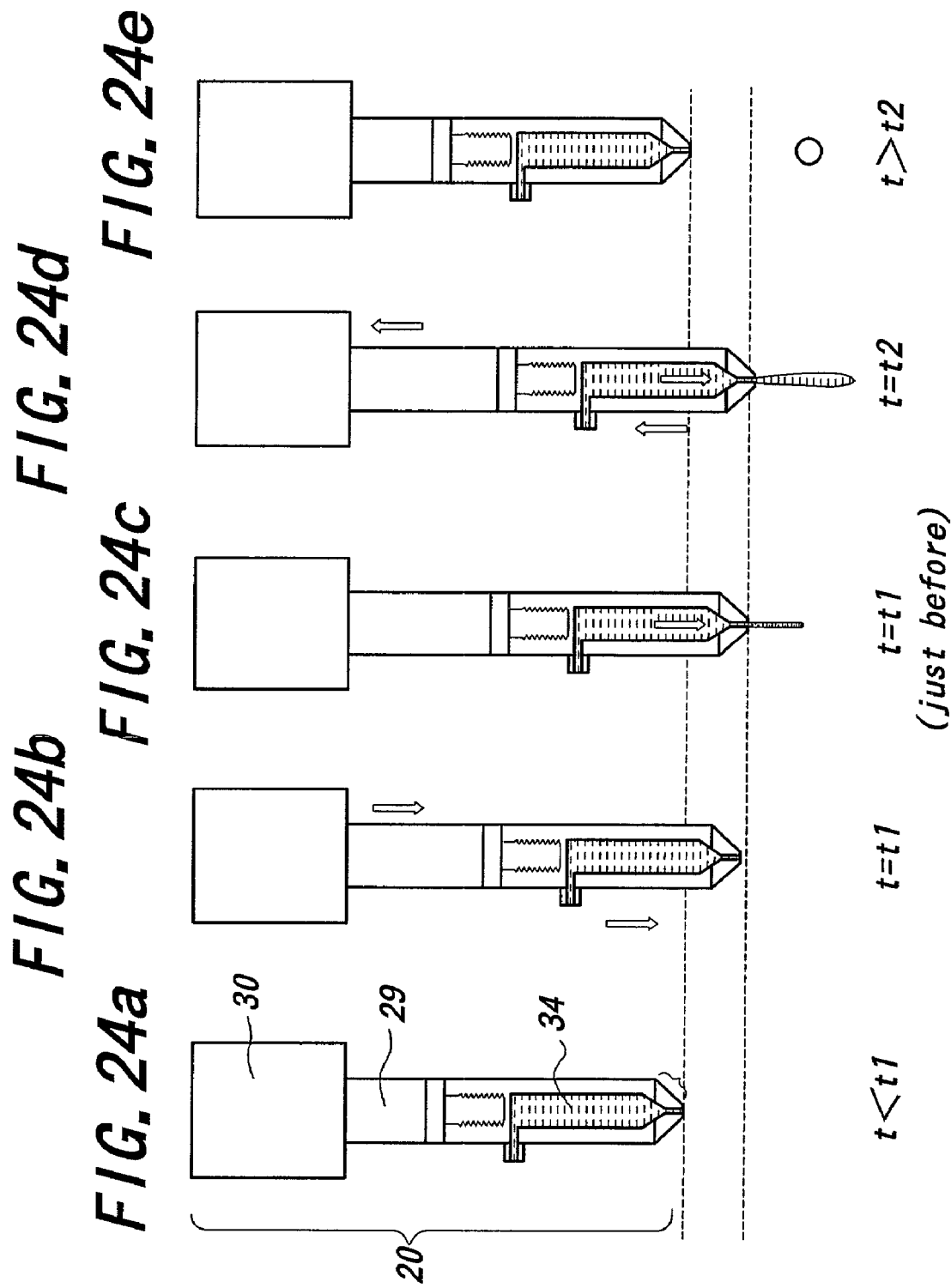
FIGS. 24(a)–(e) are explanatory views showing the dispense operation of the liquid dispense means when driving with the voltage wave form of FIG. 23 according to the third embodiment of the present invention.

FIG. 23 shows the driving voltage wave form of the laminated piezo-electric element in the second modified embodiment of the third embodiment, and FIG. 24 shows the dispensing operation of the liquid dispense means 20 in case of driving it with this voltage wave form. In the initial state of FIG. 24(a), the liquid dispense means 20 is in rest condition, when the voltage is supplied at instant t=t1 of FIG. 24(b), the liquid dispense means 20 is displaced in the downward direction on the drawing, just behind instant t=t1 of FIG. 24(c), when the voltage reaches E1, the liquid dispense means 20 stops at the position of level B. At this time, the inspection sample is dispensed from the nozzle 35 by the first inertia force acting on the inspection sample in the downward direction on the drawing. After little time, when the voltage is decreased rapidly from E1 to E0 at the instant t=t2 of FIG. 24(d), the liquid dispense means 20 is displaced to the position from level B to level A, according to this, the second inertia force acts on the inspection sample in the downward direction. Therefore, at instant t=t2, Both the first inertia force and the second inertia force act on the inspection sample, so that the inertia force acting on the inspection sample becomes larger than ones of the third embodiment and the first modified embodiment.

Therefore, in the second modified embodiment, in addition to the effect achieved by first embodiment, a lot of dispense volumes are obtained for the same driving voltage E1, thereby obtaining excellent energy efficiency.

Moreover, in the first embodiment, all of the conduit 34 were filled with the inspection sample, but it need not be necessarily assumed such a constitution, and even if the air layer 38 is formed above the conduit 34, the inspection sample can be dispensed. As in the prior art, in the technology for giving the liquid the acceleration by decreasing the volume of the conduit, when the bubble exists in the chamber, the conduit volume is decreased, and thus the bubble absorbs the generated pressure, so that the liquid cannot be dispensed, but in the present invention, regardless of the volume change in the conduit 34, whole of the conduit member 31 is displaced, and thus the inspection sample is dispensed by the inertia force generated in the liquid as a result, so that even if the bubble exists in the conduit 34, the inspection sample can be dispensed.

Moreover, according to the third embodiment, the liquid having the temperature more than the heatproof temperature of the piezo-electric element can be dispensed. In the prior art, the liquid and the piezo-electric element are contacted directly, or adjacent through the partition such as diaphragms, and thus the temperature of the liquid in the conduit is easily transmitted to the piezo-electric element, so that the temperature of the dispensing liquid was limited to the temperature below heatproof temperature of the piezo-electric element. On the contrary, in the present embodiment, the conduit 34 and the laminated piezo-electric element 29 can be set up by separating therebetween, so that the heat insulating body and the cooling means or the like are installed therebetween, and thus The temperature of the laminated piezo-electric element 29 can be kept below the heatproof temperature. Therefore, if the means for introducing the metal sample into the conduit and the means for heating the conduit are provided to the first embodiment, the molten metal having the temperature more than heatproof temperature of the laminated piezo-electric element 29, such as copper and gold, etc., can be dispensed.

Fourth Embodiment (Constitution)

Figure 25:
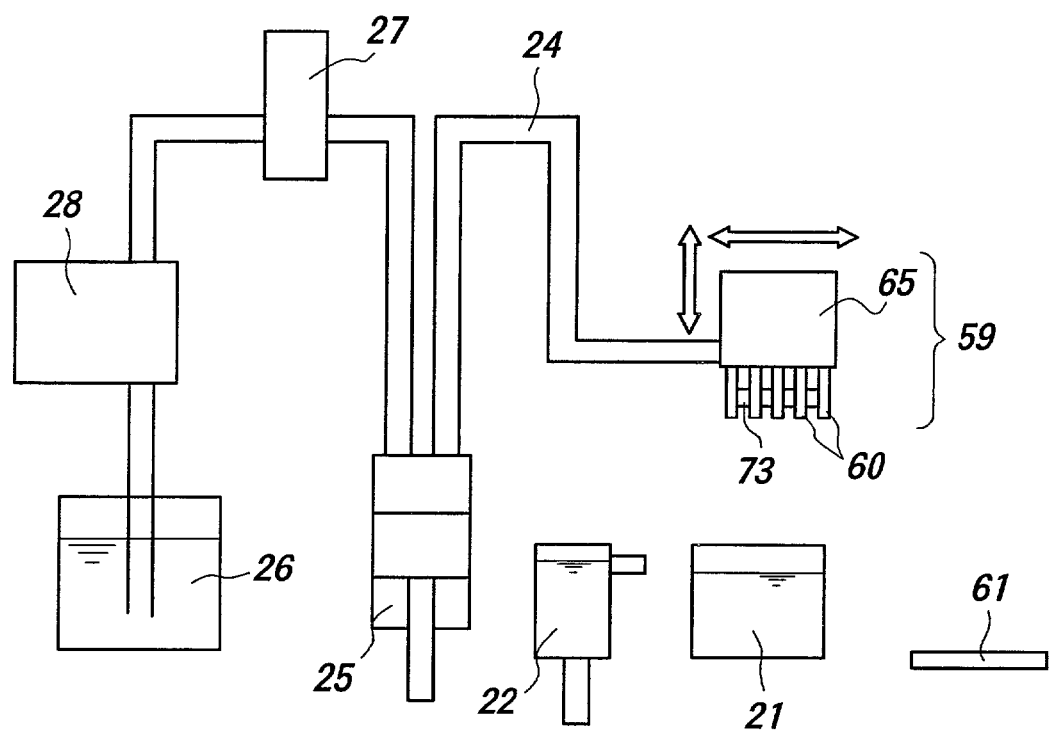
FIG. 25 is a schematic diagram of the liquid dispense apparatus according to the fourth embodiment of the embodiment of the present invention.
Figure 26:
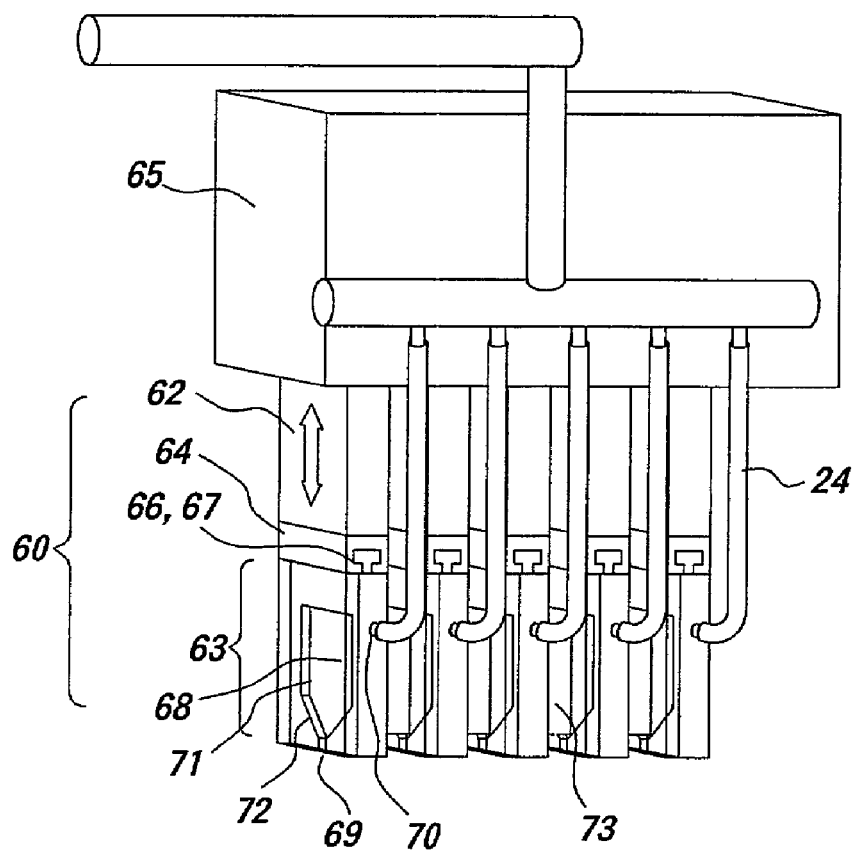
FIG. 26 is a perspective view showing the array shaped liquid dispense means being the liquid dispense means according to the fourth embodiment of the present invention.

Next, fourth embodiment is explained by FIGS. 25 and 26.

FIG. 25 shows a schematic drawing of a liquid dispensing device, and FIG. 26 is a perspective view showing an array shaped liquid dispense means 59 as the liquid dispense means in the present embodiment. The array shaped liquid dispense means 59 is constituted from plural plain plate shaped liquid dispense means 60. The individual plain plate shaped liquid dispense means 60 is connected to the syringe piston pump 25 through the Teflon piping 24, as in the first embodiment, the syringe piston pump 25 is connected to another piping which reaches the liquid supplying tank 26. Moreover, the solenoid valve 27 and the conveying pump 28 are set up between the syringe piston pump 25 and the liquid supplying tank 26. The driving structure of the syringe piston pumps 25 and the supplying routes of the washing water are similar to those of the first embodiment. Moreover, the array shaped liquid dispense means 59 is movably arranged over the washing tank 22, the inspection specimen container 21 and a reactive substrate 61 by a movable transporting member (not shown). Moreover, the reactive substrate 61 is installed on the movable transporting stand (not shown), and thus it can move to the paper plane back and forth.

The plain plate liquid dispense means 60 is constituted from a laminated piezo-electric element 62, a conduit member 63, and a connecting member 64, which connects these member 62 and 63. One end of the deviating direction of the laminated piezo-electric element 62 is secured to a trestle 65, and another edge thereof is secured to the connecting member 64. A T-shaped recess portion 66 is provided to the bottom of connecting member 64.

The conduit member 63 consists of a protrusion part 67 which engage or mate with the recess portion 66 of the connecting member 64, a conduit 68, a nozzle 69 and a liquid introducing vent 70.

The conduit 68 forms a recess on the silicon substrate by a wet etching, the Pyrex glass is formed thereon by an anodes junction. The depth of the conduit 68 is 0.1 mm–0.5 mm, and is constituted from a straight portion 71 and a taper portion 72. As for its size, the straight portion 71 has 2 mm–5 mm in width and 10 mm–3 mm in length, the taper portion 72 is formed toward the nozzle 69 from the lower end of the straight portion 71, and its tapered angle is 10 degrees–45 degrees. The conduit 34 consists of the straight portion 36 and the taper portion 37, and as for its dimension, and as for its schematic size, the straight portion 36 has $\phi$ 0.5 mm–$\phi$ 4 mm in length and 2 mm–15 mm in diameter. Nozzle 69 has a rectangular, small cross-sectional area, and the length of one arm is 0.05 mm–0.5 mm. The water repellent layer of a fluorine system material, which is low surface energy substance is provided to the end face and the outer peripheral surface of the nozzle 69.

The liquid introducing vent 70 is connected to the syringe piston pump 25 through the Teflon piping 24. The recess portion 67 is installed on the top of the conduit member 63, and the conduit member 63 and the laminated piezo-electric element 62 are connected by inserting the recess portion 67 into the recess portion 66 of the connecting member 64. The voltage of the desired wave form is supplied from the driving circuit (not shown) to the laminated piezoelectric element 62 by a lead wire or a flexible substrate. Moreover, respective plain plate liquid dispense means 60 has thin thickness of 0.5 mm–1 mm and long length of 2 mm–10 mm in the longitudinal direction, on the other hand, so that when array shaped liquid dispense means 59 is moved by the movable transporting member (not shown), the flexural vibration is generated easily. When the flexural vibration is generated, a repeated stress is applied to the base portion of the flat plate shaped liquid dispensing means 60, so that there is a danger that the joint portion with the trestle 65 peels off. In order to prevent this danger, a vibration preventing member 73 such as nitrile rubbers is secured to the side opposite to the plane, on which the conduit 68 of the conduit member 63 is formed. The vibration preventing member 73 is installed so as to contact it to the adjacent flat plate shaped liquid dispensing means 60, and thus there is an effect to control the flexural vibration of the flat plate shaped liquid dispensing means 60.

(Function)

Array shaped liquid dispense means 59 performs washing operation and sucking operation of the inspection sample as the same operation as in the first embodiment, thereby moving the reactive substrate 61 upwardly.

Figure 27:
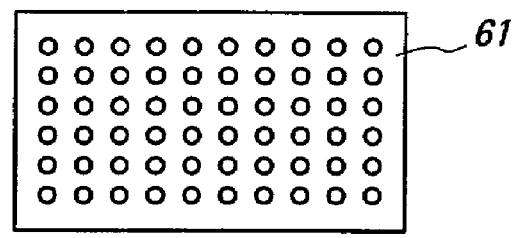
FIG. 27 is a plan view showing the inspection sample of the same size arranged in a reactive substrate in the matrix shape according to the fourth embodiment of the present invention.

Here, the voltage wave form as described in the first embodiment is supplied to the laminated piezo-electric element 62 of respective flat plate shaped liquid dispensing means 60, thereby dispensing inspection sample in the reactive substrate 61 from respective nozzles 69. After this, the inspection sample of the same size can be arranged in the reactive substrate 61 in a matrix shape as shown in FIG. 27, by dispensing the inspection sample by a similar method, while changing a relative position of the array shaped liquid dispense means 59 and the reactive substrate 61.

(Effect)

According to the present embodiment, in addition to the effect obtained by the first embodiment, a plurality of inspection samples can be dispensed on reactive substrate 61 with a high density, in a short time, by arraying the array shaped liquid dispense means 59.

Fifth Embodiment (Constitution)

Figure 28:
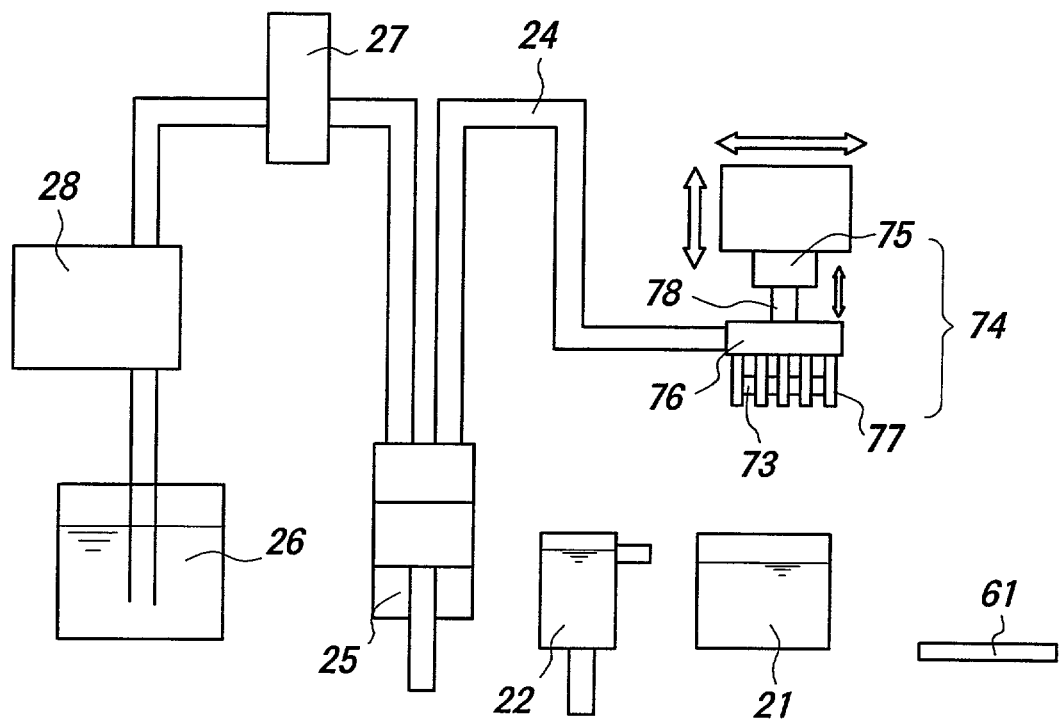
FIG. 28 is a schematic diagram showing the liquid dispense apparatus according to the fifth embodiment of the present invention.
Figure 29:
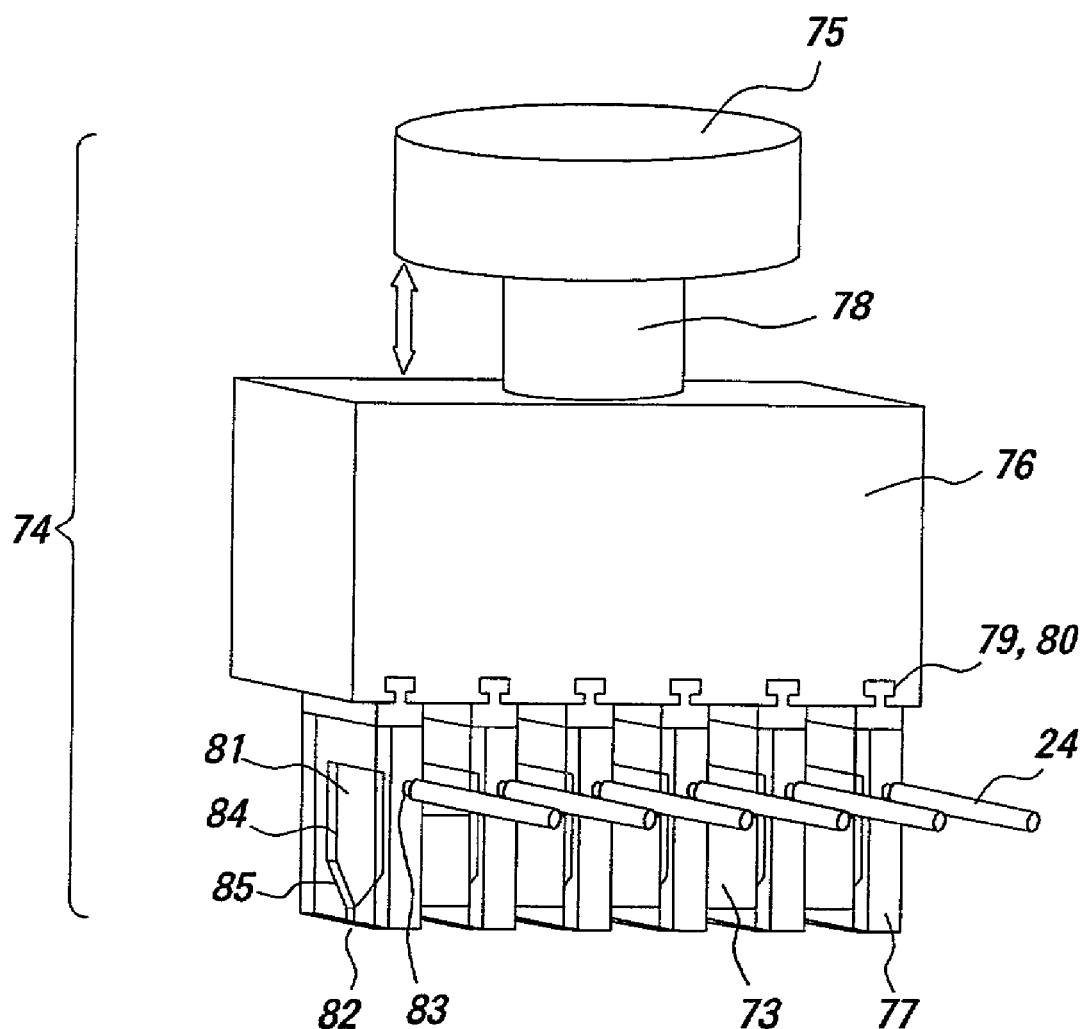
FIG. 29 is a perspective view showing the multi liquid dispense means being the liquid dispense means according to the fifth embodiment of the present invention.

Fifth embodiment of the present invention is explained with reference to FIGS. 28 and 29. FIG. 28 is a schematic diagram of a liquid dispensing device, and FIG. 29 is a perspective view of a multi liquid dispense means 74 being the liquid dispense means in the present embodiment. The multi liquid dispense means 74 comprises a solenoid piston 75, an intermediate block 76 and a plurality of plain plate shaped conduit members 77. The solenoid piston 75 can be vertically reciprocated on the drawing, so that when a given voltage is applied, a piston rod 78 is rapidly displaced to the upward direction on the drawing, and stops at the upper limit position. When the voltage is released, the piston rod 78 is displaced to the downward direction on the drawing by a built-in coil spring, and then returns to the lower limit position. One end of the solenoid piston 75 is held to the movable transporting member (not shown). Moreover, the intermediate block 76 having plural recess portions 79 is secured to the tip of the solenoid piston 75 at its bottom surface.

The plain plate shaped conduit member 77 comprises a protrusion part 80 which engages or mates with the recess portion 79 under the intermediate block 76, a conduit 81, a nozzle 82 and a liquid introducing vent 83. The conduit 81 forms a recess on the silicon substrate by a wet etching, the Pyrex glass is formed thereon by an anodes junction. The depth of the conduit 81 is 0.1 mm–0.5 mm, and is constituted from a straight portion 84 and a taper portion 85. As for its schematic size, the straight portion 84 has a width of 2 mm–5 mm and a length of 10 mm–3 mm, as well as the taper portion 85 is formed from the bottom of the straight portion 84 toward the nozzle 82, and its inclination angle is 10 degrees–45 degrees. The nozzle 82 has a rectangular and minute cross-sectional area, and the length of one arm is 0.05 mm–0.5 mm. The water repellent layer of fluororesin, which is low surface energy substance is provided to the end face and the outer peripheral surface of the nozzle 82. The protrusion part 80 is installed to the top of plain plate shaped conduit member 77, and is inserted into the recess portion 79 of the intermediate block 76, thereby connecting the plain plate shaped conduit member 77 with the intermediate block 76.

Each of the liquid introducing vent 83 of the plain plate shaped conduit member 77 is connected to the syringe piston pump 25 respectively through the Teflon piping 24, and the syringe piston pump 25 is connected to another piping, which is connected to the liquid supplying tank 26. Moreover, the solenoid valve 27 and the conveying pump 28 are located between the syringe piston pump 25 and the liquid service tank 26. Additionally, the driving structure of the syringe piston pump 25 and the supplying path of the washing water are similar to those of the first embodiment. Moreover, the multi liquid dispense means 74 is arranged and disposed over the washing tank 22, the inspection specimen container 21 and the reactive substrate 61, respectively by the movable transporting member. The reactive substrate 61 is installed to the movable transporting stand (not shown), so as to be able to move it back and forth of the paper plane.

The voltage of the desired wave form is supplied from the driving circuit (not shown) to the solenoid piston 75 laminated piezo-electric element 62 by a lead wire or a flexible substrate. Moreover, the vibration preventing member 73 is provided to each plain plate shaped conduit member 77 as in the second embodiment.

(Function)

The multi liquid dispense means 74 performs washing operation and sucking operation of the inspection sample as the same operation as in the first embodiment, thereby moving the reactive substrate 61 upwardly. Here, when a given voltage is supplied to the solenoid piston 75, the piston rod 78 rapidly moves to the upward direction on the drawing, and stops at the upper limit position. Therefore, each flat plate shaped liquid dispensing means 77 is rapidly displaced to the upward direction on the drawing with given volume, the inertia force in the downward direction acts on the inspection sample held to the conduit 81, and the inspection sample is dispensed at the same time from the nozzle 82 of all flat plate shaped liquid dispensing means 77. After this, when the voltage supplied to the solenoid piston 75 is released, the piston rod 78 is displaced downward by the coiled spring, and stops at the lower limit position. At this time, the coiled spring of the solenoid piston 75 is appropriately and previously selected, so as not to dispense the inspection sample in accordance with the inertia force acting on the inspection sample. Next, the inspection sample of the same size can be arranged on the reactive substrate 61 in the matrix shape as in FIG. 27, by dispensing the inspection sample in a similar method, while changing a relative position of the array shaped liquid dispense means 74 and the reactive substrate 61.

(Effect)

According to the present embodiment, in addition to the effect obtained by the first embodiment, individual plain plate shaped conduit member 77 can be made thin, so that the feature of making the liquid dispense means an array becomes easy, and thus a lot of inspection samples can be dispensed in a short time. In addition, the number of driving means can be decreased, so that the controller of the driving means can be simplified.

Sixth Embodiment (Constitution)

Sixth embodiment of the present invention is explained with reference to FIGS. 30 and 31. FIG. 30 shows a schematic diagram showing a liquid dispensing device, and FIG. 31 shows an enlarged view of a liquid dispense means 86.

As shown in FIG. 30, in a liquid dispensing device of the present embodiment, as in the first embodiment, the liquid dispense means 86 is connected to the syringe piston pump 25 through the Teflon piping 24, and the syringe piston pump 25 is connected to another piping, which reaches the liquid service tank 26. Moreover, the solenoid valve 27 and the conveying pump 28 are installed between the syringe piston pump 25 and the liquid supplying tank 26. In the other point, the driving structure of the syringe piston pump 25 and the supply path of the washing water are similar to the first embodiment. Moreover, the liquid dispense means 86 is arranged movably over the position of the washing tank 22, the inspection specimen container 21, a nozzle holder 87, the reactive container 23 and a nozzle separation means 88 by the movable transporting member (not shown).

The liquid dispense means 86 utilizes the laminated piezoelectric element 29 as a driving means. The one end of the laminated piezo-electric element 29 in the direction of the displacement is secured to the trestle, and a male screw member 32' is secured to another end thereof. The male screw member 32' is screwed to a female screw 90 which is provided to a conduit member 89. The conduit member 89 is formed with a metal or a hard plastic, and has a liquid introducing vent 91, a conduit 92, and a sucking vent 93. The liquid introducing vent 91 is connected to the syringe piston pump 25 through the Teflon piping 24. Moreover, the shape of the conduit 92 has a straight shape, and does not have recess and protrusion portions. Sizes of the conduit 92 are ϕ 0.5 mm–ϕ 4 mm in diameter, and 2 mm–15 mm in length, and the sucking vent 93 is ϕ 0.3 mm–ϕ 2 mm.

The outer periphery form of the conduit member 89 consists of a cylindrical section 94 and a conical section 95. The voltage of the desired wave form is supplied from the driving circuit (not shown) as a controlling means to the laminated piezo-electric element 29 by a lead wire or a flexible substrate.

The nozzle member 96 is formed with softer material than the conduit member 89 such as the Teflon resin materials and has a conical conduit 97, internally. The conical conduit 97 has the same inclination angle as that of the conical section 95 of the conduit member 89, and engages with the conical section 95 of the conduit member 89. A dispense vent 98 of ϕ 0.03 mm–ϕ 0.15 mm in the diameter has been provided to one end of the nozzle member 96. The nozzle holder 87 has a conical receiving hole, thereby holding the nozzle member 96. As shown in FIG. 31(h), the nozzle separating means 88 comprises a couple of holding members 100 having fingernail 99, and grasps the top of nozzle member 96 engaging with the conical section 95 of the conduit member 89, as shown in FIG. 31(i).

(Function)

After washing the outer peripheral surface of the conduit 92 and the conduit member 89 by the same procedure as the first embodiment, the conduit 92 and the Teflon piping 24 are filled with the washing water as shown in FIG. 31(a). Next, the piston of syringe piston pump 25 moves upward on the drawing with a given volume, thereby dispensing the washing water from the sucking vent 93. Subsequently, the piston of syringe piston pump 25 moves to the middle point again, thereby sucking a given volume of the air in the conduit 92. Next, the liquid dispense means 86 moves over the inspection specimen container 21, and the sucking vent 93 is soaked in the inspection sample in the inspection specimen container 21.

After this, the piston of the syringe piston pump 25 moves downward with a given volume, thereby sucking the inspection sample in the conduit 72. When the suck of the inspection sample is completed, an air layer 101 is formed in the conduit 92 and the Teflon piping 24 as in FIG. 31(b), thereby separating the washing water and the inspection sample by the air layer. Here, the inspection sample and the air are aspirated so as to locate a head position 102 of the aspirated inspection sample downward from the liquid introducing vent 91 by all means, thereby sucking the inspection sample and the air. Then, the liquid dispense means 86 moves over the nozzle holder 87 as shown in FIG. 31(c).

At this time, the center axis of the conduit 92 of the liquid dispense means 86 and the center axis of the nozzle member 96 held to the nozzle holder 87 are arranged so as to locate them on the same axis. Subsequent, as shown in FIG. 31(d), the liquid dispense means 86 is moved downward, and the conical section 95 of the conduit member 89 is inserted in the conical conduit 97 of the nozzle member 96 along the inner periphery surface of the nozzle member 96. Here, the conical section 95 is further pushed into the nozzle member 96 by only a given volume from the position, at which the conical section 95 of the conduit member 89 and the inner periphery surface of the nozzle member 96 are engaged to each other, thereby elastically deforming the inner periphery surface of the nozzle member 96, and depress-fitting the conical section 95 to the conical conduit 97.

Thus, the nozzle member 96 is mounted to the tip of the conduit member 89. After this, the liquid dispense means 86 is moved upward as shown in FIG. 31(e), and is moved again upward to the inspection specimen container 21. Here, as shown in FIG. 31(f), the syringe piston pump 25 is moved upward by given volume over the inspection specimen container 21, thereby dispensing the inspection sample from the dispense vent 98 of the nozzle member 96, and filling the inspection sample into the conical conduit 97 of the nozzle member 96. Next, the liquid dispense means 86 is moved over the reactive container 23 as shown in FIG. 31(g), The voltage wave form shown in the first embodiment is supplied to the laminated piezo-electric element 29, the inspection sample is dispensed in the reactive container 23 from the dispense vent 98 of the nozzle members 96. After the inspection sample of the given volume is dispensed to the reactive container 23, the liquid dispense means 86 is moved to the nozzle separation means 88, as shown in FIGS. 31(h)–(j), the nozzle member is grasped, under the condition of hanging the top of the nozzle member 96 up the fingernails 99 of a couple of holding members 100, and the liquid dispense means 86 is moved upward, thereby separating the nozzle member 96 from the conduit member 89. The separated nozzle member 96 is scrapped to the scrap container.

(Effect)

According to the present embodiment, the sucking vent 93 for sucking the inspection sample can be made large regardless of the volume of the dispensing inspection sample, so that the sucking of the inspection sample can be performed in a short time. Moreover, the suck entrance 93 can be made large, so that the flow rate of the washing water in the conduit 92 can be made fast compared with the prior art, and thus the improvement of washing of the conduit 92 becomes possible. Moreover, in the case that the nozzle blocking is generated, in the prior art, the entire liquid dispense means was only exchanged, but in the present embodiment, only the nozzle member 96 may be exchanged, so that the working hours of exchanging operation becomes shorten and the reduction of waste becomes possible.

Figure 32:
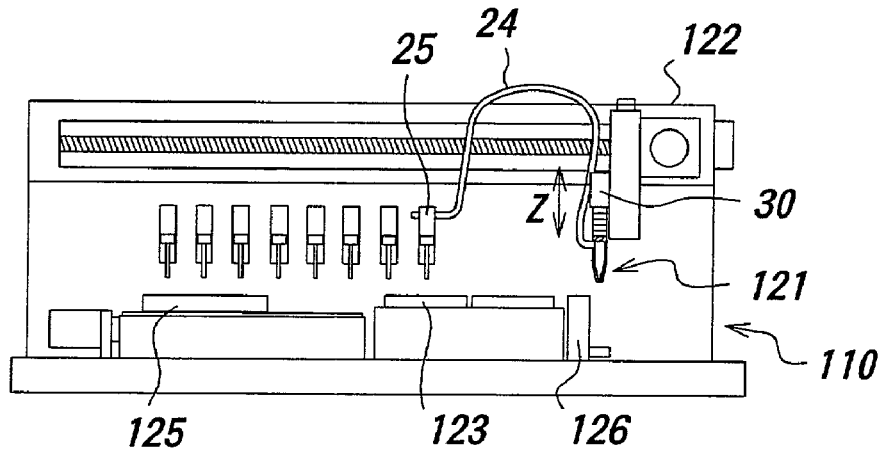
FIG. 32 is a front elevation showing the constitution of the micro array manufacturing apparatus of the seventh embodiment of the present invention.
Figure 36:
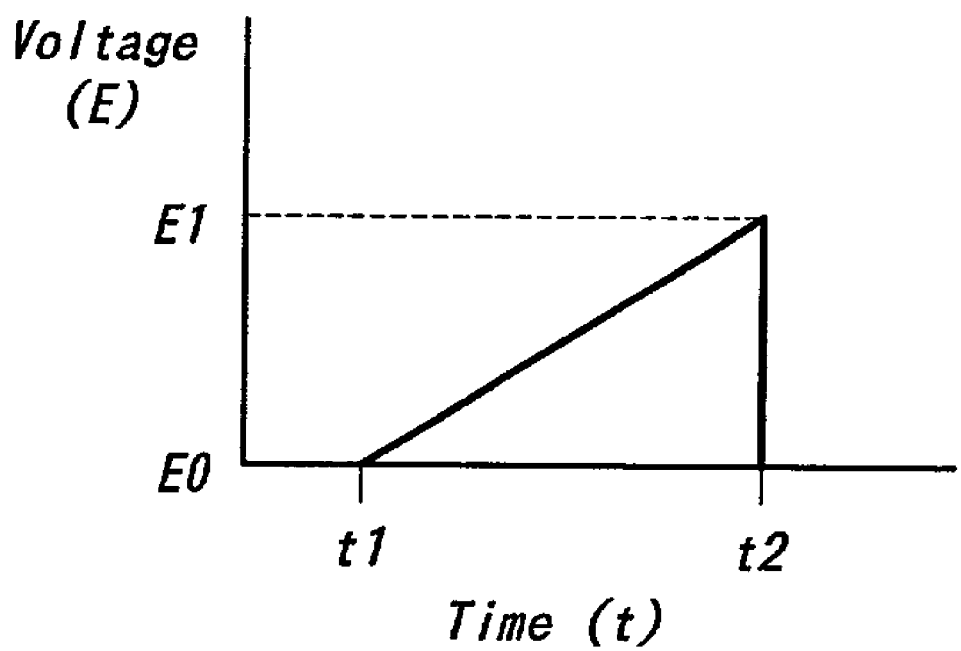
FIG. 36 is a wave form chart showing the driving wave form of the laminated piezo-electric element of the liquid dispense head of the seventh embodiment.

Next, the seventh embodiment of the present invention is explained in detail with reference to the drawings. FIG. 32 is a front view showing the constitution of the micro array manufacturing apparatus of the seventh embodiment of the present invention, FIGS. 33(a), (b) are a top plan view and a detail view of B each showing the constitution of the micro array manufacturing apparatus according to the seventh embodiment of the present invention, FIG. 34 is a perspective view of a liquid dispensing unit installed in the micro array manufacturing apparatus of the seventh embodiment, FIGS. 35(a)–(e) are explanatory views explaining the liquid dispense operation according to the liquid dispense head of the liquid dispensing unit of the first embodiment, and FIG. 36 is a wave form chart showing the driving wave form of the laminated piezo-electric element of the liquid dispense head of the seventh embodiment.

Figure 33A:
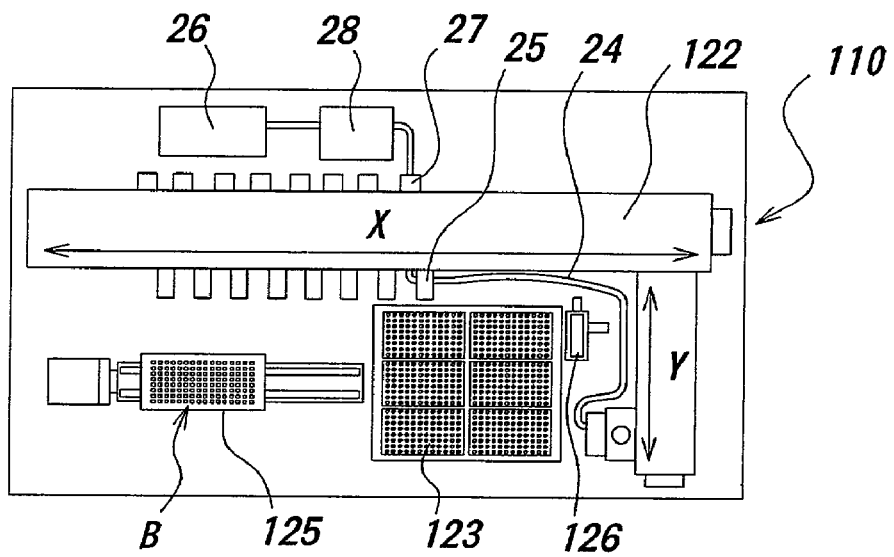
FIGS. 33(a) and (b) are a top plan view showing the constitution of the micro array manufacturing apparatus of the seventh embodiment of the present invention and a B portion detail diagram, respectively.
Figure 34:
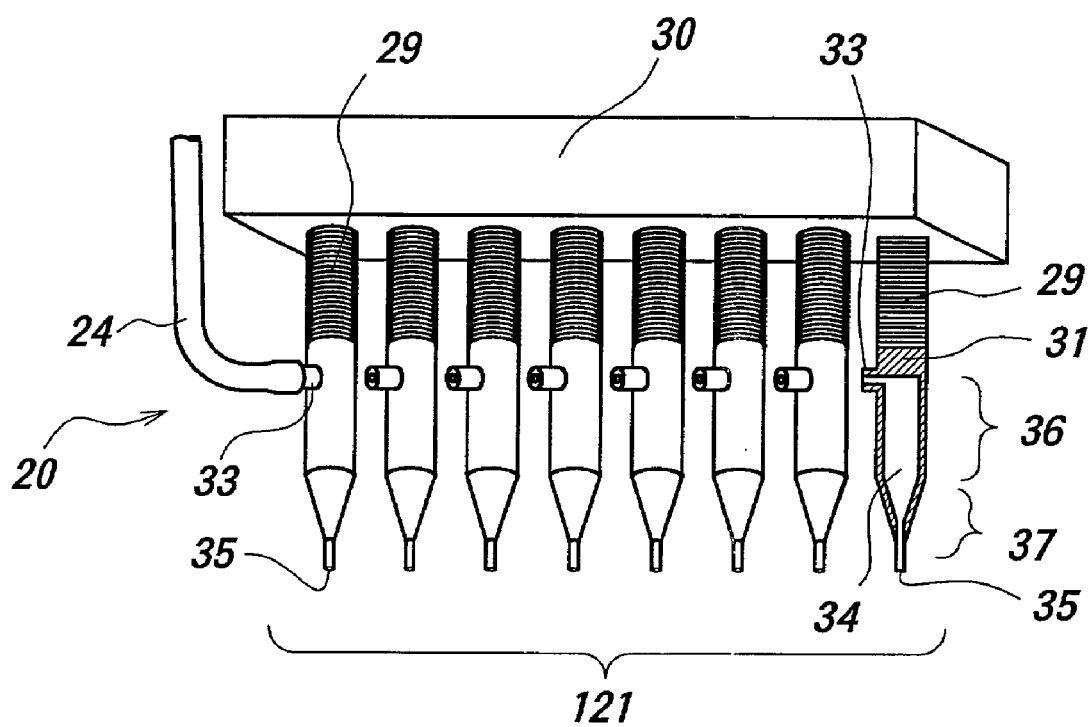
FIG. 34 is a perspective view showing the liquid dispense unit installed in the micro array manufacturing apparatus of the seventh embodiment.
Figures 35A, 35B, 35C, 35D, 35E:
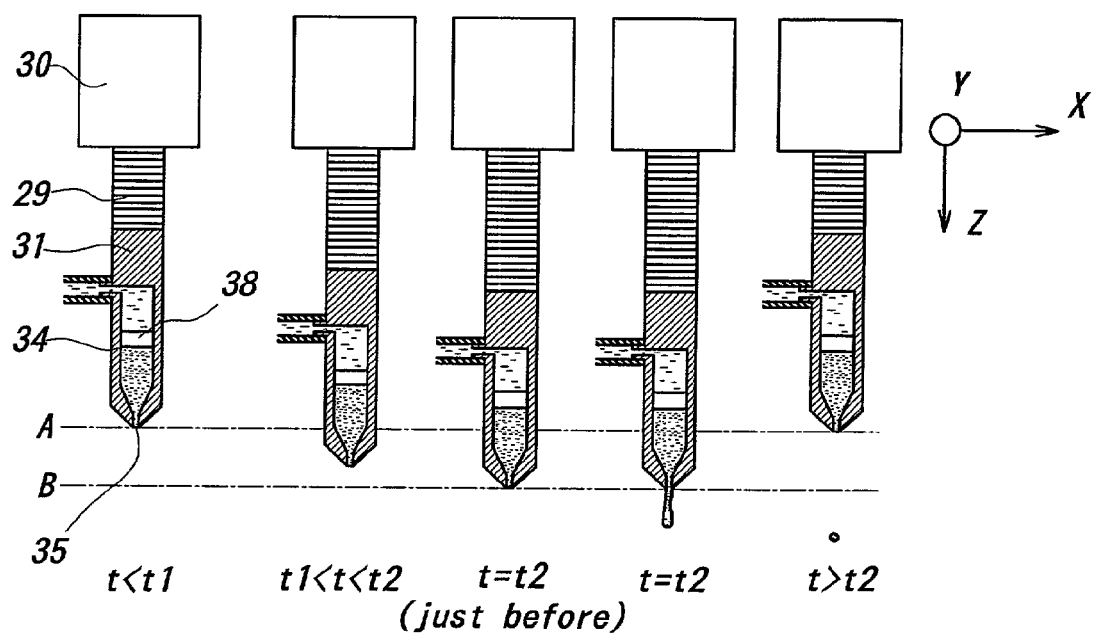
FIGS. 35(a)–(e) are explanatory views for explaining the liquid dispense operation of the liquid dispense head of the liquid dispense unit according to the seventh embodiment.

First of all, a schematic constitution of a micro array manufacturing apparatus 110 of this embodiment is explained by FIGS. 32, 33(a), (b), and 34. In the micro array manufacturing apparatus 110 of this embodiment, a liquid dispensing unit 121 consisting of eight liquid dispense heads 20 shown in FIG. 34, is installed in XYZ robot 122 (relative moving means) which can move in X, Y, and Z directions (right and left, back and forth, and vertical directions), and each liquid dispense head 20 is connected to the syringe piston pump 25 through the Teflon piping 24 (only one of right end is shown, and other pipings are omitted in the drawings).

The syringe piston pump 25 is connected to another piping in the liquid supplying tank 26 in addition to the Teflon piping 24, and the syringe piston pump 25 is connected to the liquid supplying tank 26 through the solenoid valve 27 and the conveying pump 28 by the another piping, successively. The liquid dispense head 20, the syringe piston pump 25 and the liquid supplying tank 26 are located on substantially same level. The water becoming the washing water or degassed ion exchange water is filled in the liquid supplying tank 26, so that the washing water is supplied to and fills the respective piping 24, syringe piston pump 25 and the liquid dispense head 20 by the conveying pump 28.

The laminated piezo-electric element 29 as a driving means, is provided to the upper portion of the liquid dispense head 20. The one end (upper end shown in FIG. 34) in the moving direction of the laminated piezo-electric element 29 is secured to the trestle 30, and another end (bottom end shown in FIG. 34) thereof is secured to the conduit member 31. The laminated piezo-electric element 29 moves the conduit member 31 by its displacement in the dispensing direction (Z direction) vertically. The conduit member 31 consists of the liquid introducing vent 33, the conduit 34 and the nozzle 35 as shown in the partially sectional view of the right end of FIG. 34, and the conduit 34 consists of the straight portion 36 and the taper portion 37. The liquid introducing vent 33 is connected to the syringe piston pump 25 through the Teflon piping 24. The conduit 34 has the straight portion 36 being a diameter of $\phi$ 0.5 mm–$\phi$ 4 mm, and a length of 2 mm–15 mm. Taper portion 37 is formed toward the nozzle 35 from the straight portion 36, and its inclination angle is 10 degrees–45 degrees. The nozzle 35 has a diameter of $\phi$ 0.03 mm–$\phi$ 0.15 mm, and a length of 0.05 mm–1 mm.

The water repellent layer of fluorine system material, which is low surface energy substance, is provided to the end face and the outer peripheral surface of the nozzle 35. The member between the laminated piezo-electric element 29 and the conduit 34 is formed as a rigid body, so that the volume of conduit 34 does not change by the displacement of the laminated piezo-electric element 29. Moreover, the one end of the laminated piezo-electric element 29 is secured to the trestle 30, so that the whole of conduit member 31 moves in accordance with the displacement of the laminated piezo-electric element 29. The voltage of the desired wave form described later is supplied to the laminated piezo-electric element 29 from the driving circuit (not shown) by a lead wire or a flexible substrate.

Figure 33B:
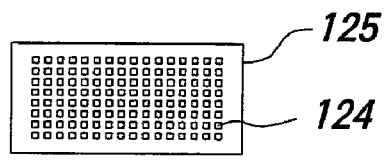

A specimen container 123 has 96 holes in total which consist of 8 rows in side×12 rows in length as shown in FIG. 33(*a*), and is installed on a base by six pieces. DNA sample solution containing a fluorescent sampled one chain DNA probe, is put in the hole of each specimen container 123. The liquid dispense head 20 of the liquid dispensing unit 121 is placed by the same pitch as a pitch of the hole of specimen container 123 of eight rows in side. Reference numeral 124 is a porous membrane filter, which is used as a substrate, and minute liquid drops of DNA sample solution are arranged in two dimensional matrix shape by the following methods. The size of the membrane filter 124 is 5 mm×5 mm–20 mm×20 mm (for example about 8 mm×8 mm), and plural pieces of filters are adsorbed on a movable stage 125 by an adsorbing member (not shown). In this embodiment, 128 membrane filters 124 are installed as shown in the detail view of FIG. 33(*b*).

Reference numeral 126 shown in FIG. 33 is a washing tank, and this liquid dispensing unit 121 is washed in the washing tank 126. The liquid dispensing unit 121 moves between the respective positions of the washing tank 126, the specimen container 123 and the membrane filter 124 by the XYZ robot 122, is positioned at the respective position and stopped.

Next, functions at sucking operation and dispensing operation in case of manufacturing the micro array by the micro array manufacturing apparatus 110 of this embodiment, are explained with reference to FIGS. 35(*a*)–(*e*) and FIG. 36.

First of all, the sucking operation is explained. The liquid dispensing unit 121 is moved over the upper part of washing tank 126, and after the nozzle 35 of the conduit member 31 of each liquid dispense head 20 is soaked in the washing tank 126 only by 1 mm–2 mm, and the solenoid valve 27 is opened, the washing water in the liquid supplying tank 26 is sent to the conduit by the conveying pump 28, and then the inner periphery surface of the conduit 34 and the outer peripheral surface and the end face of the nozzle 35 are washed with the washing water. In such a way, during sending the washing water, the syringe piston pump 25 is moved to the middle point, thereby filling the washing water in the syringe piston pump 25. Under such a condition, after shutting the solenoid valve 27, the liquid dispense head 20 is moved upward the washing tank 126. Subsequently, the piston of the syringe piston pump 25 is moved upward by only given volume, thereby dispensing the washing water from the nozzle 35. After this, the piston of the syringe piston pump 25 is moved to the middle point, thereby sucking the given volume of the air is aspirated in the conduit 34.

Next, the liquid dispensing unit 121 is moved over the upper part of the specimen container 123, and DNA liquor in the hole of the specimen container 123 is aspirated in the conduit 34 by the nozzle 35 of the conduit member 31 of each liquid dispense head 20. Therefore, DNA sample solution aspirated in the conduit is separated from the washing water by the air layer 38 shown in FIG. 35(*a*). After finishing the sucking of the DNA sample solution, the liquid dispensing unit 121 is moved over the membrane filter 124, is positioned at this position and is stopped, and then, the DNA sample solution is dispensed on the membrane filter 124 by following methods, by changing a relative position in the XY plane of the membrane filter 124 and liquid dispensing unit 121, while minute adjusting the dispense position.

Next, the dispensing operation is explained. While supplying the voltage of the wave form shown in FIG. 36 to the laminated piezo-electric element 29 of the liquid dispense head 20, a position of the vertical direction at the tip of the nozzle 35 of the conduit member 31 with voltage E=E0 at instant t<t1 of FIG. 35(*a*) is assumed as A, the liquid dispense head 20 is slowly displaced to the downward direction on the drawing in accordance with a gradual rising of the voltage in instant t1<t<t2 of FIG. 35(*b*), the displacement corresponding to the voltage E1 is generated in the laminated piezoelectric element 29 just before the instant t=t2 of FIG. 35(*c*) and the tip of the nozzle 35 descends to the position of B by the displacement. Moreover, the volume of the stroke between the above position A and position B is for example 1–10 μm.

Subsequently, the voltage E instantaneously decreases to E0 in instant t=t2 of FIG. 35(*d*). According to the abrupt decrease of the voltage E, the conduit member 31 of the liquid dispense head 20 is changed from the descending to the ascending and moves in the upward direction on the drawing rapidly. At this time, the inertia force in the downward direction on the drawing acts on the DNA sample solution in the conduit 34 of the conduit member 31, thereby generating the flow to the downward direction. By this flow, the pressure of the tip portion of the conduit 34 is increased, and the liquid drops of DNA sample solution are dispensed on the membrane filter 124 from the end face of the nozzle 35. In this case, the volume of the dispensing liquid varies according to the nozzle diameter, the physical properties value of DNA sample solution, and the driving voltage wave form, etc, but it is about 0.1 nl–0.3 μl. Subsequently, the liquid dispense head 20 returns to an initial position at the instant t>t2 of FIG. 35(*e*).

The diameters of the liquid drop of the dispensed DNA sample solution are φ 50 μm–φ 200 μm, and thus such liquid drops are dispensed on the membrane filter 124 at intervals of about 150 μm-400 μm. In this case, after dispensing DNA sample solution from eight liquid dispense heads 20 on each membrane filter 124, simultaneously, the liquid dispensing unit 121 is again moved upward the upper part of washing tank 126, and then DNA sample solution remained in the conduit 34 is exhausted, thereby washing the conduit 34 and the outer peripheral surface thereof. Thereafter, while changing a relative position of the membrane filter 124 and the conduit member 31 of the liquid dispense head 20 in the XY plane by the XYZ robot 122, the above described sucking operation, the dispensing operation, and the washing operation are repeated, and minute liquid drops of DNA sample solution are dispensed on the membrane filter 124 in two dimensional matrix shape with 75 μm–400 μm intervals. In that case, the membrane filter 124 has a porous quality, so that the dispensed DNA sample solution infiltrates membrane filter 124, and is held therein. Thus, DNA probe array is made as a micro array.

According to this embodiment, DNA sample solution is dispensed from the nozzle 35 of the tip of the conduit member 31 of the liquid dispense head 20 by inertia force. the volume of the inertia force does not change, even if the bubble exists in the conduit 34, so that DNA sample solution of a constant volume is always dispensed at a constant speed, regardless of presence of the bubble in the conduit 34, and thus DNA probe array having a uniform spot diameter can be manufactured with the positional precision of an excellent dispense. Moreover, the pressure of tip portion of the conduit 34 increases by the vertical movement of the conduit member 31 of the liquid dispense head 20, so that the dispensing speed of DNA sample solution can be increased.

Moreover, in this embodiment, a single-strand DNA probe was used as a sample of the micro array, but the present invention is not limited to this, as a sample constituting an array, DNA, RNA or PNA or the like, which have, for example, ligand, receptor for the ligand, oligo or polypeptide having a specific amino acid sequence, various ferments, various proteins, antigens, antibodies, and specific base sequences, may be used.

Moreover, in this embodiment, the porous membrane filter 124 was used as a substrate, but the present invention is not limited to this, for example, a slide glass, a silicon substrate, a plastic board, and a ceramics board, etc. may be used. However, in order to prevent the contamination between adjacent probes, it is preferable that the probe dispensed on the substrate is secured to the given position, but in order to secure the sample of the probe on the solid substrate, the functional group capable of being reacted mutually may be combined to both the probe and the substrate. Some of such a method are already opened to the public, for example, thiol (-SH) radical is combined to the end of the probe, and process is so performed that the surface of the substrate has the maleimide radical, therefore, following process may be performed, that the probe is secured on the substrate as the thiol group of the probe supplied to the surface of the substrate reacts with the maleimide radical on the surface of the substrate. Moreover, the epoxy radical is introduced on the substrate, and it may make the amino group in the end of the probe react.

Figure 37:
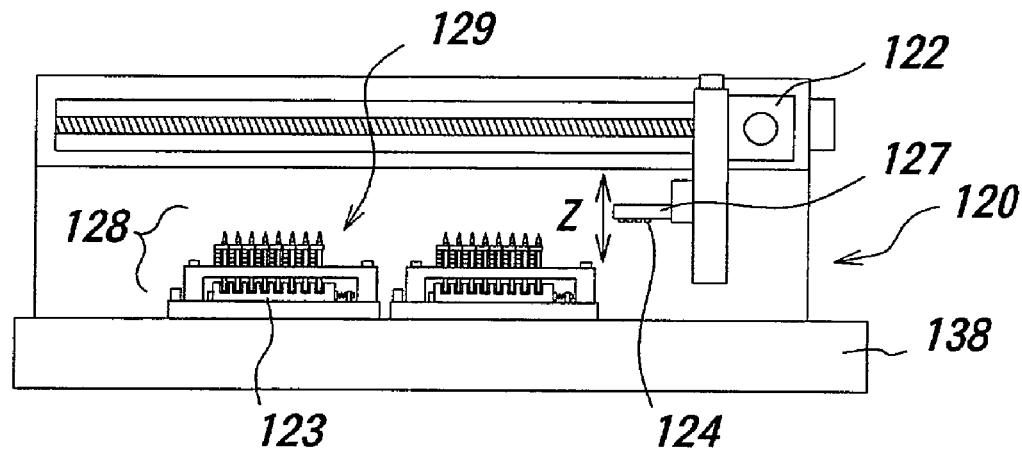
FIG. 37 is a front elevation showing the constitution of the micro array manufacturing apparatus according to the eighth embodiment of the present invention.
Figure 38:
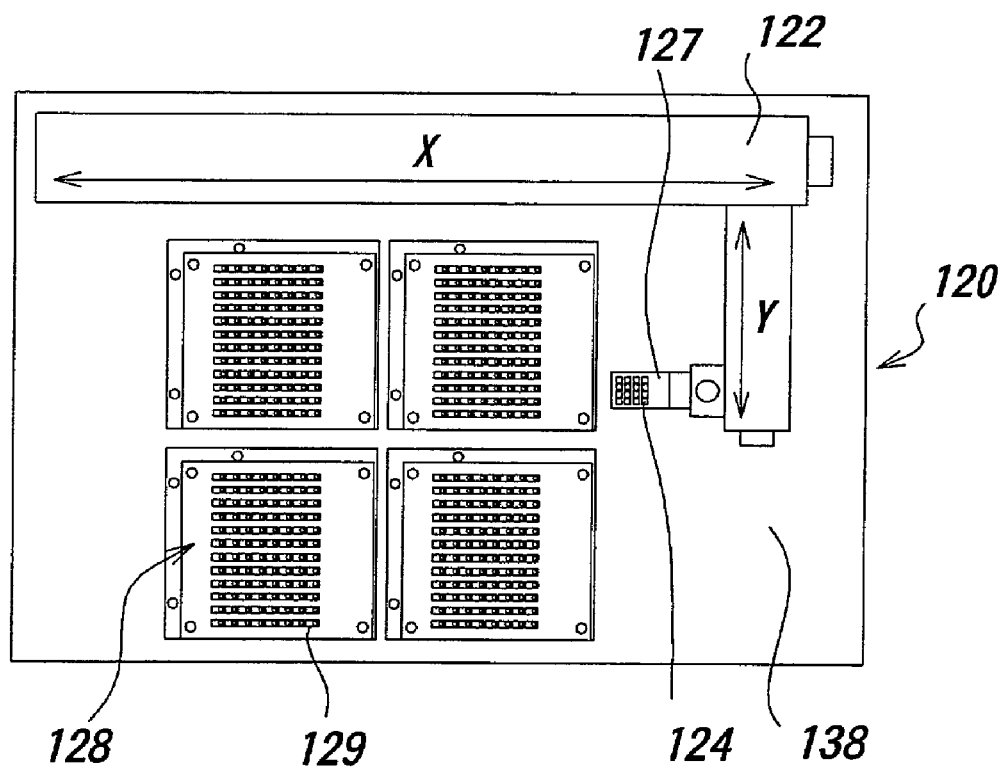
FIG. 38 is a top plan view showing the constitution of the micro array manufacturing apparatus of the eighth embodiment of the present invention.

FIGS. 37 and 38 are a front view and a top plan view each showing the constitution of the micro array manufacturing apparatus of the eighth embodiment of the present invention, respectively, and the same numeral has been put on the same section as the seventh embodiment. In the micro array manufacturing apparatus 120 of this embodiment, plural pieces of the membrane filters 124 are adsorbed and secured to lower surface of a filter base 127 supported by the XYZ robot 122, and the top and bottom relation of the membrane filter 124 is reversed to the seventh embodiment. The reference numeral 128 of FIG. 37 is a dispensing unit, in which plural liquid dispense head 129 and specimen container 123 were integrated. Hereafter, a detailed constitution of the dispensing unit 128 is explained with reference to FIG. 39.

Figure 39:
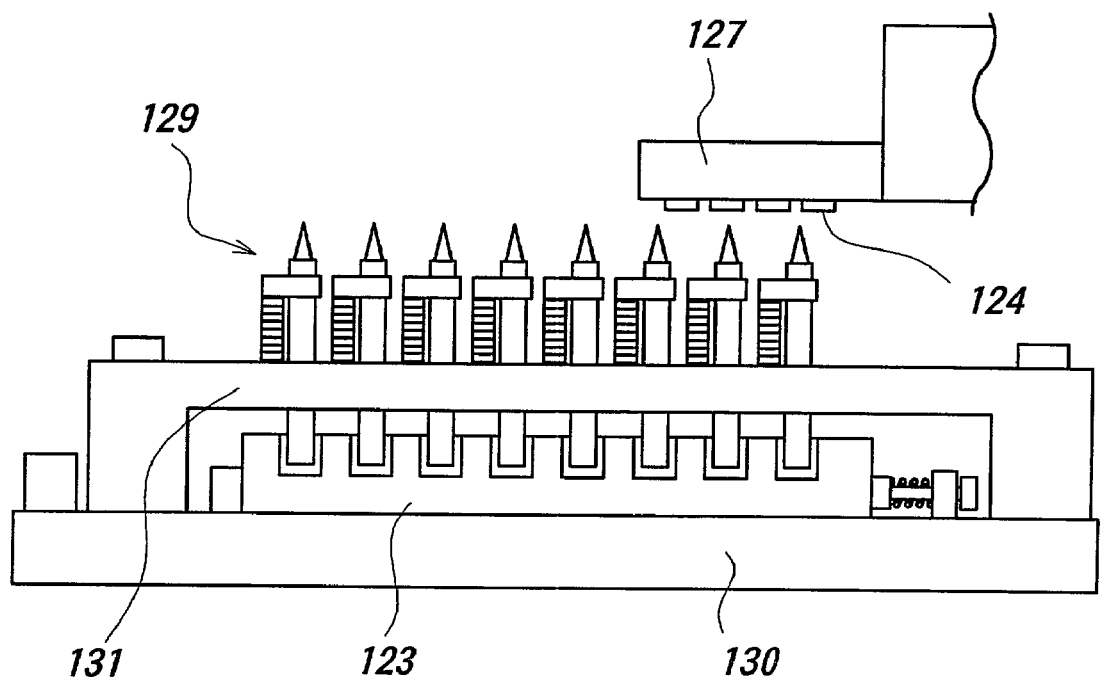
FIG. 39 is a side view showing a detailed constitution of the dispense unit of the eighth embodiment.

In FIG. 39, the specimen container 123 is a liquid container for supplying DNA sample solution to the conduit member 132, and DNA sample solution is so accommodated that the liquid surface is opened to the atmosphere. The specimen container 123 has 96 holes in total which consist of 8 rows in side×12 rows in length, and DNA sample solution containing a fluorescent labeled DNA probe of single chain, is put in respective holes, and secured to certain position of the unit base 130. Reference numeral 131 is a dispense head base being the base of liquid dispense head 129, and has (⊐) shaped cross-sectional form of piece, and further secured to the unit base 130 with the screw so as to cover the specimen container 123.

Figure 40A:
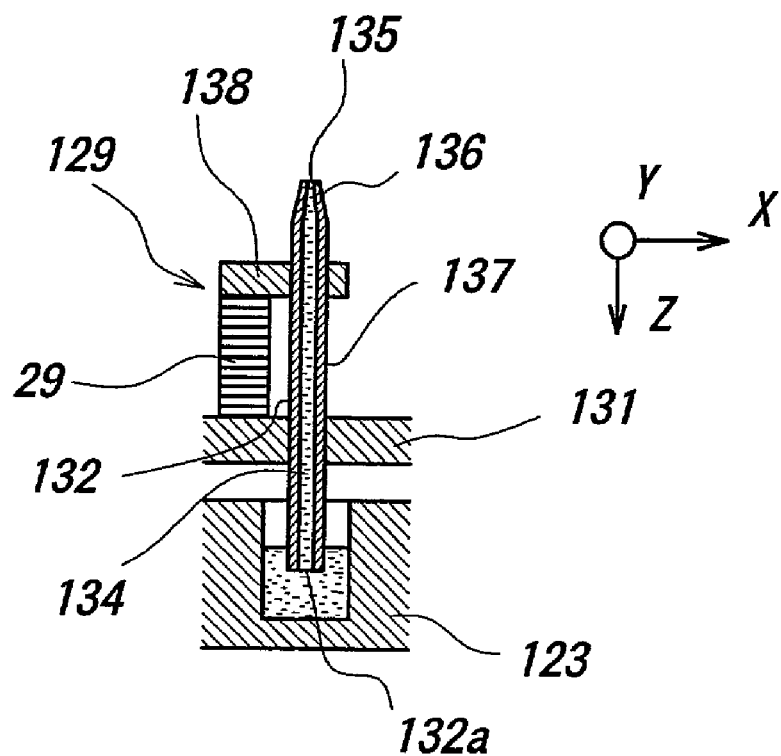
FIG. 40(a) is a cross-sectional view showing the liquid dispense head of the eighth embodiment.

As shown in the cross-sectional view of FIG. 40(a), the liquid dispense head 129 is constituted by the conduit member 132, the laminated piezo-electric element 29 which is the driving means for driving the conduit member 132, and a connecting member 133 for connecting the laminated piezo-electric element 29, and the conduit member 132 rigidly. The conduit 134 is formed therein the conduit member 132, and the nozzle 135 is formed in the top of the conduit 134 of the conduit member 132. The nozzle 135 comprises a straight portion 137 and a taper portion 136. Moreover, Titania is coated on the inner surface of the conduit 134, thereby obtaining a surface of hydrophilic property. A bottom 132a of conduit 134 of conduit member 132 is an opened end, the bottom 132a is soaked with the liquor of in the hole of specimen container 123, so that DNA sample solution in respective holes of the specimen container 123 are aspirated in the conduit 134 by the capillary action, and are held. Particularly, the surface energy of the conduit 134 has increased by titania, so that DNA sample solution is aspirated up in the conduit 134 by the capillary action, thereby filling all in the conduit 134.

The one end (the bottom end shown in FIG. 40(a)) in the polarized direction of the laminated piezo-electric element 29 is adhered and secured to the dispense head base 131, and another end (the upper end shown in FIG. 40(a)) is secured to the conduit member 132 through the connecting member 133, so that the whole of the conduit member 132 moves to the dispensing direction (vertical and Z directions on the drawing), by expanding and contracting the laminated piezo-electric element 29. The one end (upper end shown in FIG. 34) in the moving direction of the laminated piezo-electric element 29 is secured to the trestle 30, and another end (bottom end shown in FIG. 34) thereof is secured to the conduit member 31. The laminated piezo-electric element 29 moves the conduit member 31 by its displacement in the dispensing direction (Z direction) vertically. 96 liquid dispense heads 129 in total are provided to one dispense unit 128, and such four dispense units 128 are arranged at a given position of base 138. Moreover, the desired voltage is supplied from the driving circuit (not shown) to respective laminated piezo-electric elements 29 through the connector and the lead wire.

The membrane filter 124 is arranged and moved over the respective dispense units 128 by the XYZ robot 122, and a relative position of membrane filter 124 in the XY plane and the liquid dispense head 129 of respective dispense unit 128 is adjusted thereby. The distance of the membrane filter 124 and the nozzle 135 of the liquid dispense head 129 is about 0.5 mm–2 mm.

Next, functions at the sucking operation and the dispensing operation in case of manufacturing the micro arrays by the micro array manufacturing apparatus 120 of this embodiment are explained by using FIGS. 37 and 38.

In FIG. 37, first of all, the membrane filter 124 is moved to the position at about 1 mm over the desired liquid dispense head 129 and positioned and secured by the XYZ robot 122. Next, the driving voltage wave form of the above described FIG. 4 is supplied to the laminated piezo-electric element 29 of the liquid dispense head 129, and DNA sample solution held to the conduit 134 is dispensed to the membrane filter 124 arranged there-over from the nozzle 135 as minute liquid drops by similar function to the above seventh embodiment.

At this time, the drop speed of the dispensing liquid drop decreases by the influence of gravity, but the speed of the liquid drop dispensed to the distance (for example, about 1 mm) between the nozzle 135 and the membrane filter 124 is very fast with 3 m/s–10 m/s, so that the dispensed droplets arrived at the membrane filter 124, surely. Moreover, the size of the liquid drop of the dispensing DNA sample solution is $\phi$ 30 μm–$\phi$ 300 μm in the diameter, and the membrane filter 124 is porous, so that the dispensed DNA sample solution penetrate the membrane filter 124 and is held therein.

Subsequent, while moving the membrane filter 124 in the XY direction shown in FIG. 7 in the two dimensional matrix shape, the DNA sample solution is dispensed from the liquid dispense head 129 at respective positions thereof, by arranging a minute spot of the DNA sample solution on the membrane filter 124 in the matrix shape with high density, thereby forming the DNA probe array.

Moreover, if the moving procedure of membrane filter 124 and the dispense timing of liquid dispense head 129 are previously decided, the above operation can be automatically performed. Moreover, the dispense unit 128 can be used repeatedly by decomposing it into the specimen container 123 and the dispense head base 131 and by washing them. Moreover, if a plurality of dispense unit 128 are prepared, the washing of the dispense unit and the manufacturing of the probe array can be performed at the same time.

According to this embodiment, the effect of the above seventh embodiment can be obtained, and the following effects can be obtained. That is, in this embodiment, the end portion opposite to the end portion positioned at the nozzle 135 of the conduit 134 in the conduit member 132 is made an open end 132*a*, this open end 132*a* is soaked in such a manner that the liquid surface is opened to the atmosphere in the DNA sample solution of the specimen container 123 in which the DNA sample solution is accommodated, and thus the DNA sample solution is supplied by the capillary phenomenon by the specimen container 123 in the conduit member 132, thereby holding it in the conduit 134, so that the DNA sample solution need not be aspirated, and the liquid supply mechanism (the piping, the syringe piston pump, and the solenoid valve, etc.) to introduce the DNA sample solution into the conduit 134 in the conduit member 132 becomes unnecessary and thus the downsizing of the apparatus and the decrease in cost of the apparatus become possible.

In addition, in this embodiment, the cleaning process of the conduit 134 and the dispensing step of the DNA sample solution can be performed concurrently by another step. so that the probe array can be made in a short time. Moreover, in the above seventh embodiment, the acceleration added to the washing water and DNA sample solution held in the Teflon piping 24 and the conduit 34, respectively, in case of moving the liquid dispensing unit 121, so that as a result of changing the meniscus in the nozzle 35, there is a possibility to influence the dispensing precision, but according to this embodiment, The portion for holding the DNA sample solution is always secured, so that the meniscus does not change, and thus the dispense precision can be improved. Moreover, in this embodiment, the liquid dispense head 129 is secured and the membrane filter 124 is moved, so that the moving speed of the membrane filter 124 can be made faster than the first embodiment, and the manufacturing time of the micro array can be made shorter than the first embodiment.

Figure 40B:
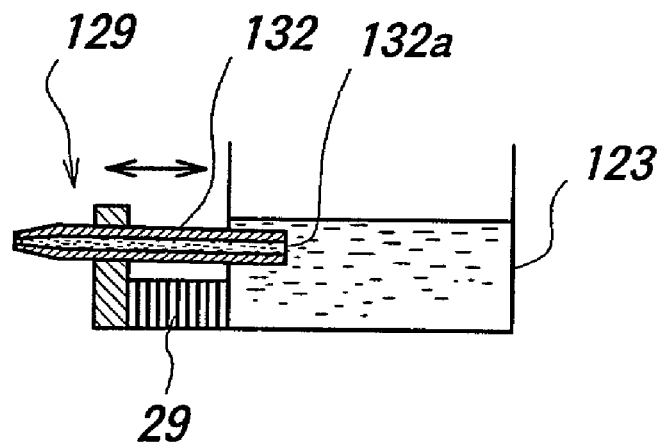
FIG. 40(b) is a cross-sectional view showing the modified embodiment thereof.

Moreover, in this embodiment, the conduit member 132 is arranged almost vertically on the liquid surface of the specimen container 123 as shown in FIG. 40(*a*), but the present invention is not limited thereto, for example, as shown in FIG. 40(*b*), the constitution that the conduit member 132 is arranged smallly slantwise to the side of the specimen container 123 with some angles for a horizontal plane., may be provided. In that case, the supporting direction of the liquid dispense head 129 according to the XYZ robot 122 must be changed accordingly, too.

Figure 41:
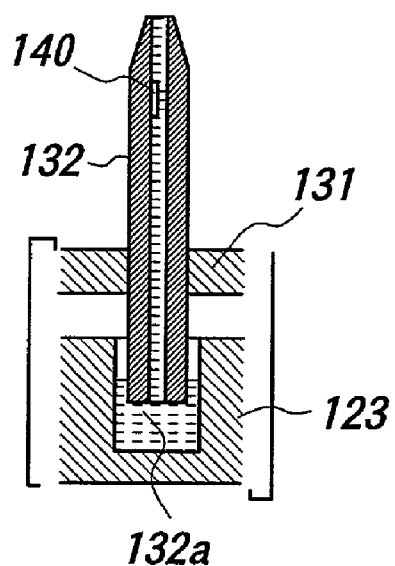
FIG. 41 is a cross-sectional view showing the first modification of the eighth embodiment of the present invention.
Figure 42:
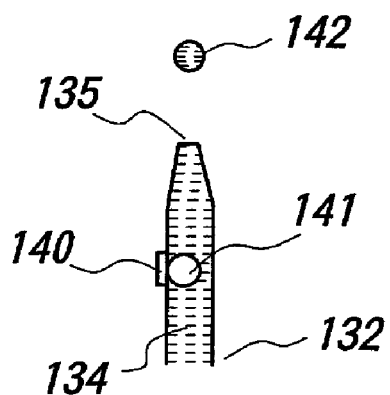
FIG. 42 is a cross-sectional view showing the second modification of the eighth embodiment of the present invention.

Moreover, the dispense head of this embodiment is not limited to the above described liquid dispense head 129, for example, as shown in FIG. 41, a resistive heat body 140 may be provided with the conduit member 132. In FIG. 41, the conduit member 132 is secured to the dispense head base 131, and the voltage is supplied to the resistor heat body 140 from the electric circuit (not shown). When the voltage is supplied to the resistor heat body 140, as shown in FIG. 42, a bubbles 141 is generated in the conduit 134, and the pressure is caused in the conduit 134 by the bubble 141, thereby dispensing the minute DNA sample solution from the nozzle 135 as a liquid drop 142.

Figure 43:
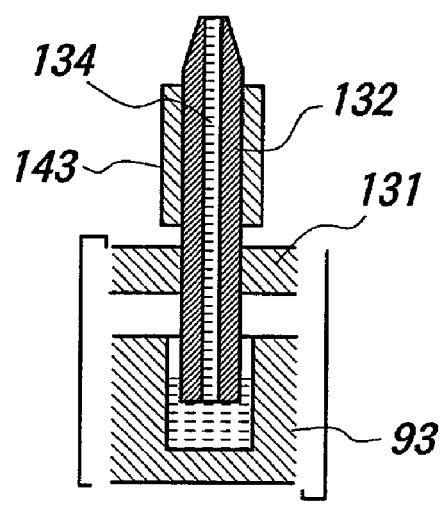
FIG. 43 is a cross-sectional view showing the third modification of the eighth embodiment of the present invention.
Figure 44:
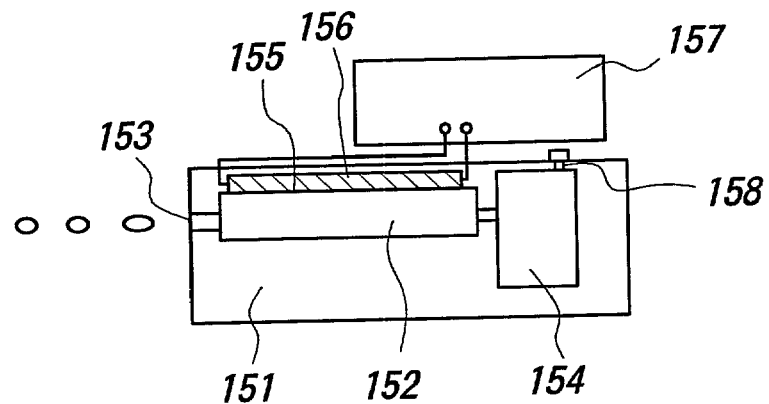
FIG. 44 is a schematic block diagram in which the main portion of the main portion of liquid pipetting apparatus as a conventional technology, that is, ink jet type nanopipette is shown by the cross-section.
Figure 45:
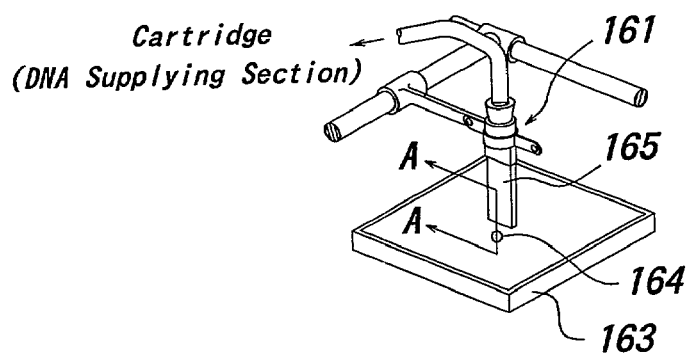
FIG. 45 is a perspective view explaining the manufacturing method of the conventional micro array.
Figure 46:
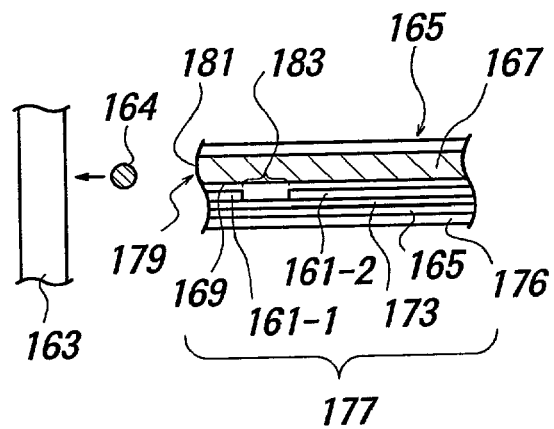
FIG. 46 is a cross-sectional view on the A—A line of FIG. 45.

Moreover, for example, in addition thereto, as shown in FIG. 43, the dispensing head, in which the cylindrical piezo-electric element 148 is engaged and bonded to the conduit member 132, may be used. In FIG. 43, the cylindrical piezo-electric element 143 is provided with electrode to the inner periphery surface and the outer peripheral surface thereof, and the inner periphery surface is polarized in negative and the outer peripheral surface is polarized in positive. Moreover, the voltage is supplied from the driving circuit (not shown). Therefore, when supplying the voltage, the cylindrical piezo-electric element 143 is displaced in the direction to which the inner diameter shrinks, thereby shrinking the conduit member 132. As a result, the pressure in the conduit 134 is increased, and the minute DNA sample solution is dispensed from the nozzle 135 as a droplet.

What is claimed is:

1. A liquid pipetting apparatus for dispensing a minute amount of liquid comprising:
   at least one conduit member for holding the liquid therein and having a dispensing end;
   a driving means;
   an actuator associated with the at least one conduit member, and
   a controller configured to supply voltage to the driving means to move the at least one conduit member and dispense the liquid from a dispensing end thereof when the at least one conduit member is moved in a dispensing direction by voltage applied to the actuator, temporarily stopped, and then moved in a direction opposite the dispensing direction of the liquid by a decrease in the voltage applied to the actuator, wherein dispensing substantially occurs while concurrently moving the conduit member in the direction opposite the dispensing direction.

2. A liquid pipetting apparatus as claimed in claim 1, wherein the controller is configured to actuate the driving means to accelerate the at least one conduit member in the dispensing direction at a first magnitude and in the direction opposite to the dispensing direction at a second magnitude.

3. A liquid pipetting apparatus as claimed in claim 2, wherein the first magnitude of acceleration is less than the second magnitude of acceleration.

4. A liquid pipetting apparatus as claimed in claim 1, wherein after being moved in the direction opposite to the dispensing direction of the liquid, the controller is configured to actuate the driving means to move the at least one conduit member to a specific position in order to dispense the liquid held within the at least one conduit member from one end thereof.

5. A liquid pipetting apparatus as claimed in claim 1, wherein the controller is configured to actuate the driving means for the at least one conduit member to repeat the movement in the dispensing direction of the liquid and the movement in the direction opposite to the dispensing direction of the liquid.

6. A liquid pipetting apparatus as claimed in claim 1, wherein the liquid is held in the at least one conduit member before the controller actuates the driving means to move the at least one conduit member in the direction opposite to the dispensing direction of the liquid.

7. A liquid pipetting apparatus as claimed in claim 1, further comprising a washing means capable of washing the at least one conduit member.

8. A liquid pipetting apparatus as claimed in claim 7, wherein the washing means contains a pump for sending to the at least one conduit member a cleaning solution capable of washing the at least one conduit member.

9. A liquid pipetting apparatus as claimed in claim 1, wherein the at least one conduit member holds the liquid in the inside thereof and contains a dispensing vent at a distal end thereof to dispense the liquid held in the at least one conduit member through the dispensing end.

10. A liquid pipetting apparatus as claimed in claim 9, wherein an inner portion of the at least one conduit member has a taper shape, of which the cross-sectional area becomes smaller as the inner portion approaches the dispensing vent.

11. A liquid pipetting apparatus as claimed in claim 1, wherein the actuator includes a piezoelectric element.

12. A liquid pipetting apparatus as claimed in claim 1, wherein the at least one conduit member is connected to the actuator detachably.

13. A liquid pipetting apparatus as claimed in claim 1, wherein the at least one conduit member comprises a plurality of conduit members.

14. A liquid dispensing method for dispensing a minute amount of liquid from one end of at least one conduit member for holding the liquid, comprising:
 providing the liquid pipetting apparatus of claim 1;
 holding the liquid in the at least one conduit member; and
 dispensing the liquid held in the at least one conduit member from one end thereof, when the conduit member is moved in the direction opposite to the dispensing direction of the liquid by the decrease in voltage applied to the actuator associated with the at least one conduit member.

15. A liquid dispensing method as claimed in claim 14, further including stopping the conduit member between moving the conduit member in a dispensing direction of the liquid and moving the conduit member in the direction opposite the dispensing direction of the liquid.

16. A liquid dispensing method as claimed in claim 14, further including moving the at least one conduit member in the dispensing direction of the liquid and wherein after being moved in the dispensing direction of the liquid, the at least one conduit member is moved in the opposite direction to the dispensing direction of the liquid.

17. A liquid dispensing method as claimed in claim 16, wherein at the time that the at least one conduit member moves in the dispensing direction of the liquid and at the time that the at least one conduit member moves in the direction opposite to the dispensing direction of the liquid the acceleration of the at least one conduit member is different in magnitude.

18. A liquid dispensing method as claimed in claim 17, wherein an acceleration in the at least one conduit member at the time the at least one conduit member is moved in the direction opposite to the dispensing direction of the liquid is larger than an acceleration at time the at least one conduit member is moved in the dispensing direction of the liquid.

19. The method of claim 14, further comprising washing the at least one conduit member after the at least one conduit member is moved in the direction opposite to the dispensing direction of the liquid.

20. The method of claim 14, further comprising washing the at least one conduit member after the at least one conduit member is moved in the direction opposite to the dispensing direction of the liquid.

* * * * *